US010870810B2

(12) United States Patent
Steill et al.

(10) Patent No.: US 10,870,810 B2
(45) Date of Patent: Dec. 22, 2020

(54) METHOD AND SYSTEM FOR CONVERTING ASSOCIATED GAS

(71) Applicant: Advanced Green Innovations, LLC, Chandler, AZ (US)

(72) Inventors: Jason S. Steill, Phoenix, AZ (US); Adam Smith, Coolidge, AZ (US); Dean C. Hoaglan, Gilbert, AZ (US); Scott V. Johnson, Scottsdale, AZ (US); David L. Grottenthaler, Phoenix, AZ (US); Robert Terry Kennon, Kamuela, HI (US); Michael R. Johnson, Tempe, AZ (US); Steven K. Eddy, Chandler, AZ (US); Kenneth Losch, Chandler, AZ (US); Charles Robert Rapier, Chandler, AZ (US); Jay K. Neutzler, Leander, TX (US)

(73) Assignee: PROTEUM ENERGY, LLC, Chandler, AZ (US)

( * ) Notice: Subject to any disclaimer, the term of this patent is extended or adjusted under 35 U.S.C. 154(b) by 164 days.

(21) Appl. No.: 16/041,706

(22) Filed: Jul. 20, 2018

(65) Prior Publication Data
US 2019/0024003 A1 Jan. 24, 2019

Related U.S. Application Data

(60) Provisional application No. 62/535,189, filed on Jul. 20, 2017.

(51) Int. Cl.
C10L 3/10 (2006.01)
C01B 3/34 (2006.01)
(Continued)

(52) U.S. Cl.
CPC ............. *C10L 3/10* (2013.01); *C01B 3/346* (2013.01); *C01B 3/38* (2013.01); *C01B 3/388* (2013.01);
(Continued)

(58) Field of Classification Search
CPC .............. C07C 9/04; C01B 2203/0233; C01B 2203/1241; C01B 3/38; C01B 3/382;
(Continued)

(56) References Cited

U.S. PATENT DOCUMENTS 1,794,232 A 2/1931 Humphrey
2,135,694 A 11/1938 Bardwell et al.
(Continued)

FOREIGN PATENT DOCUMENTS

DE 69120740 11/1996
DE 69219084 7/1997
(Continued)

OTHER PUBLICATIONS

Product literature from Austro Energy Systems Int. AG for "Gas reformer AES3000", 25 pages, Dec. 19, 2014, Vienna, Austria.
(Continued)

*Primary Examiner* — Imran Akram
(74) *Attorney, Agent, or Firm* — Marshall, Gerstein & Borun LLP

(57) ABSTRACT

A volume of natural gas including a volume of methane and a volume of other alkanes may be cleaned of the other alkanes using a steam reformer system to create synthesis gas.

51 Claims, 5 Drawing Sheets

(51) Int. Cl.
  *C01B 3/38*   (2006.01)
  *C07C 1/12*   (2006.01)
  *C07C 1/04*   (2006.01)
  *C10L 3/08*   (2006.01)
  *C07C 7/148*  (2006.01)

(52) U.S. Cl.
  CPC ............. *C07C 1/0485* (2013.01); *C07C 1/12* (2013.01); *C07C 7/14866* (2013.01); *C10L 3/08* (2013.01); *C01B 2203/0233* (2013.01); *C01B 2203/0415* (2013.01); *C01B 2203/0475* (2013.01); *C01B 2203/0495* (2013.01); *C01B 2203/062* (2013.01); *C01B 2203/1258* (2013.01); *C01B 2203/16* (2013.01); *C10L 2290/04* (2013.01); *C10L 2290/06* (2013.01); *C10L 2290/148* (2013.01); *C10L 2290/562* (2013.01); *C10L 2290/58* (2013.01); *C10L 2290/60* (2013.01)

(58) Field of Classification Search
  CPC .... C01B 2203/0445; C01B 2203/1276; C01B 3/32; C01B 2203/0205; C01B 2203/0227; C01B 2203/1235; C01B 2203/1258; C10L 3/08; H01M 8/0612
  See application file for complete search history.

(56) References Cited

U.S. PATENT DOCUMENTS

| | | |
|---|---|---|
| 2,151,329 A | 3/1939 | Page et al. |
| 2,397,899 A | 4/1946 | Witkiewicz |
| 2,433,255 A | 12/1947 | Atwell |
| 2,623,596 A | 12/1952 | Whorton et al. |
| 2,692,274 A | 10/1954 | Kolbel et al. |
| 2,729,291 A | 1/1956 | Haverfield |
| 2,875,832 A | 3/1959 | Martin et al. |
| 2,880,801 A | 4/1959 | Crump |
| 3,130,026 A | 4/1964 | Becker |
| 3,193,006 A | 7/1965 | Lewis |
| 3,213,015 A | 10/1965 | Atkinson et al. |
| 3,379,505 A | 4/1968 | Holmes et al. |
| 3,415,634 A | 12/1968 | Dent et al. |
| 3,421,671 A | 1/1969 | Daves et al. |
| 3,442,332 A | 5/1969 | Keith |
| 3,453,835 A | 7/1969 | Hochgesand |
| 3,511,624 A | 5/1970 | Humphries et al. |
| 3,576,899 A | 4/1971 | Ishiguro et al. |
| 3,586,621 A | 6/1971 | Pitchford et al. |
| 3,615,164 A | 10/1971 | Baker |
| 3,625,665 A | 12/1971 | Thompson |
| 3,642,460 A | 2/1972 | Thompson |
| 3,737,291 A | 6/1973 | Lhonore et al. |
| 3,825,490 A | 7/1974 | Vachuda |
| 3,838,994 A | 10/1974 | Aldridge |
| 3,870,738 A | 3/1975 | Yamamoto et al. |
| 3,888,043 A | 6/1975 | Child et al. |
| 3,917,467 A | 11/1975 | Toida et al. |
| 3,930,812 A | 1/1976 | Harris et al. |
| 3,938,968 A | 2/1976 | White et al. |
| B521,985 I5 | 3/1976 | Leibgott |
| 3,958,956 A | 5/1976 | Goeke |
| 3,975,172 A | 8/1976 | Ranke |
| 3,992,876 A | 11/1976 | Aguet |
| 4,005,996 A | 2/1977 | Hausberger et al. |
| 4,026,355 A | 5/1977 | Johnson et al. |
| 4,070,165 A | 1/1978 | Colton |
| 4,098,587 A | 7/1978 | Krar et al. |
| 4,098,589 A | 7/1978 | Buswell et al. |
| 4,104,201 A | 8/1978 | Banks et al. |
| 4,109,701 A | 8/1978 | Hilberath et al. |
| 4,127,392 A | 11/1978 | Watson et al. |
| 4,130,575 A | 12/1978 | Jorn |
| 4,133,825 A | 1/1979 | Stroud et al. |
| 4,147,142 A | 4/1979 | Little et al. |
| 4,150,962 A | 4/1979 | Colton |
| 4,203,950 A | 5/1980 | Sederquist |
| 4,205,961 A | 6/1980 | Moller et al. |
| 4,298,694 A | 11/1981 | Skov |
| 4,319,964 A | 3/1982 | Katz et al. |
| 4,320,802 A | 3/1982 | Garbo |
| 4,370,223 A | 1/1983 | Bose |
| 4,383,837 A | 5/1983 | Smith |
| 4,545,976 A * | 10/1985 | Osman .................... C01B 3/382 423/650 |
| 4,604,215 A | 8/1986 | McCorquodale |
| 4,747,858 A | 5/1988 | Gottier |
| 4,793,919 A | 12/1988 | McCorquodale |
| 4,941,330 A | 7/1990 | Williamson |
| 5,026,934 A | 6/1991 | Bains et al. |
| 5,112,527 A | 5/1992 | Kobylinski |
| 5,139,541 A | 8/1992 | Edlund |
| 5,207,928 A | 5/1993 | Lerner |
| 5,217,506 A | 6/1993 | Edlund et al. |
| 5,224,350 A | 7/1993 | Mehra |
| 5,229,089 A | 7/1993 | Ramachandran et al. |
| 5,259,870 A | 11/1993 | Edlund |
| 5,266,283 A | 11/1993 | Friesen et al. |
| 5,266,540 A | 11/1993 | Menicagli et al. |
| 5,281,254 A | 1/1994 | Birbara et al. |
| 5,295,350 A * | 3/1994 | Child ...................... F01K 23/068 60/780 |
| 5,393,325 A | 2/1995 | Edlund |
| 5,498,278 A | 3/1996 | Edlund |
| 5,645,626 A | 7/1997 | Edlund et al. |
| 5,718,881 A | 2/1998 | Sederquist et al. |
| 5,769,165 A | 6/1998 | Bross et al. |
| 5,769,926 A | 6/1998 | Lokhandwala et al. |
| 5,775,308 A | 7/1998 | Headley |
| 5,861,137 A | 1/1999 | Edlund |
| 5,997,594 A | 12/1999 | Edlund et al. |
| 6,048,472 A * | 4/2000 | Nataraj .................... C01B 3/36 252/373 |
| 6,098,396 A | 8/2000 | Wen et al. |
| 6,114,400 A | 9/2000 | Nataraj et al. |
| 6,136,222 A | 10/2000 | Friesen et al. |
| 6,152,995 A | 11/2000 | Edlund |
| 6,221,117 B1 | 4/2001 | Edlund et al. |
| 6,232,352 B1 * | 5/2001 | Vidalin .................... C01B 3/384 518/700 |
| 6,319,306 B1 | 11/2001 | Edlund et al. |
| 6,368,742 B2 | 4/2002 | Fisher et al. |
| 6,375,906 B1 | 4/2002 | Edlund et al. |
| 6,376,113 B1 | 4/2002 | Edlund et al. |
| 6,383,670 B1 | 5/2002 | Edlund et al. |
| 6,402,818 B1 | 6/2002 | Sengupta |
| 6,419,728 B1 | 7/2002 | Edlund |
| 6,451,464 B1 | 9/2002 | Edlund et al. |
| 6,458,189 B1 | 10/2002 | Edlund et al. |
| 6,465,118 B1 | 10/2002 | Dickman et al. |
| 6,494,937 B1 | 12/2002 | Edlund et al. |
| 6,495,277 B1 | 12/2002 | Edlund et al. |
| 6,527,980 B1 | 3/2003 | Roden |
| 6,537,352 B2 | 3/2003 | Edlund et al. |
| 6,547,858 B1 | 4/2003 | Edlund et al. |
| 6,562,111 B2 | 5/2003 | Edlund et al. |
| 6,564,579 B1 | 5/2003 | McCartney |
| 6,569,227 B2 | 5/2003 | Edlund et al. |
| 6,596,057 B2 | 7/2003 | Edlund et al. |
| 6,616,841 B2 | 9/2003 | Cho et al. |
| 6,632,270 B2 | 10/2003 | Edlund et al. |
| 6,635,149 B1 | 10/2003 | Campbell et al. |
| 6,667,128 B2 | 12/2003 | Edlund |
| 6,719,831 B2 | 4/2004 | Edlund et al. |
| 6,719,832 B2 | 4/2004 | Edlund et al. |
| 6,723,156 B2 | 4/2004 | Edlund et al. |
| 6,740,205 B2 | 5/2004 | Molintas |
| 6,758,101 B2 | 7/2004 | Valentine |
| 6,767,389 B2 | 7/2004 | Edlund et al. |
| 6,780,395 B2 | 8/2004 | Narayan |
| 6,783,741 B2 | 8/2004 | Edlund et al. |
| 6,811,908 B2 | 11/2004 | Edlund et al. |
| 6,818,335 B2 | 11/2004 | Edlund et al. |

(56) References Cited

U.S. PATENT DOCUMENTS

| | | |
|---|---|---|
| 6,824,593 B2 | 11/2004 | Edlund et al. |
| 6,835,481 B2 | 12/2004 | Dickman et al. |
| 6,858,341 B2 | 2/2005 | Edlund |
| 6,869,707 B2 | 3/2005 | Edlund et al. |
| 6,878,474 B2 | 4/2005 | Dickman et al. |
| 6,890,672 B2 | 5/2005 | Dickman et al. |
| 6,953,497 B2 | 10/2005 | Edlund et al. |
| 6,979,507 B2 | 12/2005 | Edlund et al. |
| 6,994,927 B2 | 2/2006 | Edlund et al. |
| 7,005,113 B2 | 2/2006 | Edlund et al. |
| 7,008,708 B2 | 3/2006 | Edlund et al. |
| 7,052,530 B2 | 5/2006 | Edlund et al. |
| 7,090,816 B2 | 8/2006 | Malhotra et al. |
| 7,101,421 B2 | 9/2006 | Edlund et al. |
| 7,135,048 B1 | 11/2006 | Edlund et al. |
| 7,147,677 B2 | 12/2006 | Edlund |
| 7,192,562 B1 | 3/2007 | Towler et al. |
| 7,195,663 B2 | 3/2007 | Edlund et al. |
| 7,201,783 B2 | 4/2007 | Edlund |
| 7,208,241 B2 | 4/2007 | Edlund et al. |
| 7,250,231 B2 | 7/2007 | Edlund |
| 7,258,946 B2 | 8/2007 | Edlund |
| 7,264,710 B2 | 9/2007 | Hokari et al. |
| 7,297,183 B2 | 11/2007 | Edlund et al. |
| 7,306,735 B2 | 12/2007 | Baggott et al. |
| 7,368,194 B2 | 5/2008 | Dickman et al. |
| 7,368,195 B2 | 5/2008 | Edlund et al. |
| 7,390,587 B2 | 6/2008 | Dickman et al. |
| 7,410,531 B2 | 8/2008 | Edlund et al. |
| 7,442,748 B2 | 10/2008 | Cole et al. |
| 7,470,293 B2 | 12/2008 | Edlund et al. |
| 7,476,455 B2 | 1/2009 | Edlund |
| 7,485,381 B2 | 2/2009 | Dickman et al. |
| 7,601,302 B2 | 10/2009 | Edlund et al. |
| 7,632,321 B2 | 12/2009 | Edlund |
| 7,632,322 B2 | 12/2009 | Edlund |
| 7,641,795 B2 | 1/2010 | Taylor et al. |
| 7,659,019 B2 | 2/2010 | Edlund |
| 7,678,951 B2 | 3/2010 | Chretien |
| 7,682,718 B2 | 3/2010 | Dickman et al. |
| 7,736,596 B2 | 6/2010 | Edlund et al. |
| 7,771,882 B2 | 8/2010 | Edlund et al. |
| 7,789,941 B2 | 9/2010 | Edlund et al. |
| 7,819,955 B2 | 10/2010 | Edlund et al. |
| 7,828,864 B2 | 11/2010 | Edlund et al. |
| 7,846,569 B2 | 12/2010 | Edlund et al. |
| 7,866,161 B2 | 1/2011 | Mahlanen et al. |
| 7,939,211 B2 | 5/2011 | Edlund et al. |
| 7,977,000 B2 | 7/2011 | Edlund |
| 7,981,172 B2 | 7/2011 | Edlund et al. |
| 7,985,510 B2 | 7/2011 | Edlund et al. |
| 8,021,446 B2 | 9/2011 | Adams et al. |
| 8,038,748 B2 | 10/2011 | Edlund |
| 8,067,575 B2 | 11/2011 | Edlund et al. |
| 8,070,840 B2 | 12/2011 | Diaz et al. |
| 8,133,626 B2 | 3/2012 | Edlund et al. |
| 8,221,928 B2 | 7/2012 | Kivisaari et al. |
| 8,273,139 B2 | 9/2012 | Malhotra et al. |
| 8,461,216 B2 | 6/2013 | Clomburg, Jr. et al. |
| 8,470,059 B2 | 6/2013 | Clomburg, Jr. et al. |
| 8,486,167 B2 | 7/2013 | Okada et al. |
| 8,557,451 B2 | 10/2013 | Edlund et al. |
| 8,609,738 B2 | 12/2013 | Mamedov et al. |
| 8,696,772 B2 | 4/2014 | Edlund et al. |
| 8,956,428 B2 | 2/2015 | Carnell et al. |
| 8,961,627 B2 | 2/2015 | Edlund |
| 9,011,580 B2 | 4/2015 | Edlund |
| 9,162,888 B2 | 10/2015 | Okada et al. |
| 9,187,324 B2 | 11/2015 | Edlund |
| 2001/0045061 A1 | 11/2001 | Edlund et al. |
| 2002/0041837 A1 | 4/2002 | Edlund et al. |
| 2002/0071976 A1 | 6/2002 | Edlund |
| 2002/0114984 A1 | 8/2002 | Edlund et al. |
| 2003/0167690 A1 | 9/2003 | Edlund et al. |
| 2003/0168381 A1 | 9/2003 | Hokari et al. |
| 2003/0192251 A1 | 10/2003 | Edlund et al. |
| 2003/0223926 A1 | 12/2003 | Edlund et al. |
| 2003/0223931 A1 | 12/2003 | Narayan |
| 2004/0081867 A1 | 4/2004 | Edlund |
| 2004/0081868 A1 | 4/2004 | Edlund |
| 2004/0099138 A1 | 5/2004 | Karode et al. |
| 2004/0148942 A1 | 8/2004 | Pont et al. |
| 2004/0160061 A1 | 8/2004 | Rouse et al. |
| 2004/0197616 A1 | 10/2004 | Edlund et al. |
| 2005/0188616 A1 | 9/2005 | Bizjak et al. |
| 2006/0037476 A1 | 2/2006 | Edlund et al. |
| 2006/0081524 A1 | 4/2006 | Sengupta et al. |
| 2006/0090397 A1 | 5/2006 | Edlund et al. |
| 2006/0216562 A1 | 9/2006 | Edlund et al. |
| 2006/0242902 A1* | 11/2006 | Tautz ................... B01J 8/0214 48/127.9 |
| 2007/0010589 A1* | 1/2007 | Pearson .................. C10K 1/32 518/702 |
| 2007/0062116 A1 | 3/2007 | Edlund et al. |
| 2007/0172402 A1 | 7/2007 | Palo et al. |
| 2007/0274904 A1 | 11/2007 | Popham et al. |
| 2008/0031809 A1 | 2/2008 | Norbeck et al. |
| 2008/0115669 A1 | 5/2008 | Edlund et al. |
| 2008/0138677 A1 | 6/2008 | Edlund |
| 2008/0176118 A1 | 7/2008 | Edlund et al. |
| 2008/0187797 A1 | 8/2008 | Edlund |
| 2008/0222954 A1 | 9/2008 | Adams et al. |
| 2008/0305034 A1* | 12/2008 | Edlund ................. B01J 8/0285 423/652 |
| 2009/0260287 A1 | 10/2009 | Lau |
| 2010/0064887 A1 | 3/2010 | Edlund et al. |
| 2010/0162626 A1* | 7/2010 | Clomburg, Jr. ........ B01J 19/249 48/197 FM |
| 2010/0261074 A1 | 10/2010 | Edlund et al. |
| 2011/0250518 A1 | 10/2011 | Edlund et al. |
| 2011/0256459 A1 | 10/2011 | Edlund |
| 2011/0256491 A1 | 10/2011 | Edlund et al. |
| 2011/0262323 A1* | 10/2011 | Rappas .................... C10L 3/08 423/63 |
| 2011/0294905 A1* | 12/2011 | Robinson ................ C10L 3/12 518/700 |
| 2012/0058403 A1 | 3/2012 | Edlund et al. |
| 2012/0134888 A1* | 5/2012 | Blevins .................... C01B 3/02 422/162 |
| 2012/0161079 A1* | 6/2012 | Filippi .................... C01B 3/34 252/374 |
| 2012/0208903 A1 | 8/2012 | Gafney |
| 2013/0011301 A1 | 1/2013 | Edlund |
| 2013/0090505 A1 | 4/2013 | Catchpole |
| 2013/0129609 A1 | 5/2013 | Basini et al. |
| 2014/0065020 A1 | 3/2014 | Edlund et al. |
| 2014/0065021 A1 | 3/2014 | Edlund |
| 2014/0345320 A1 | 11/2014 | Xuan et al. |
| 2015/0005398 A1* | 1/2015 | Chakravarti ............ C10G 2/30 518/702 |
| 2015/0119478 A1* | 4/2015 | Bowe ...................... C01B 3/34 518/702 |
| 2015/0122128 A1 | 5/2015 | Edlund |
| 2015/0241399 A1 | 8/2015 | Li et al. |
| 2015/0284651 A1 | 10/2015 | Stuermer et al. |
| 2016/0289143 A1* | 10/2016 | Duggal ................ F01K 25/103 |
| 2016/0340595 A1* | 11/2016 | Matteucci ................ C10L 3/10 |
| 2017/0022056 A1* | 1/2017 | Christensen ............ C10L 3/103 |

FOREIGN PATENT DOCUMENTS

| | | |
|---|---|---|
| DE | 69730071 | 8/2005 |
| DE | 60035418 | 3/2008 |
| EP | 0036268 | 9/1981 |
| EP | 0193716 A2 | 9/1986 |
| EP | 3607007 A1 | 9/1987 |
| EP | 0532491 | 3/1993 |
| EP | 0570185 | 11/1993 |
| EP | 0652042 | 5/1995 |
| EP | 0718031 | 6/1996 |
| EP | 0470822 | 7/1996 |
| EP | 0546808 | 4/1997 |
| EP | 0783919 | 7/1997 |

(56) References Cited

FOREIGN PATENT DOCUMENTS

| | | |
|---|---|---|
| EP | 1010942 | 2/2003 |
| EP | 0800852 | 8/2004 |
| EP | 1272759 | 10/2004 |
| EP | 1516663 | 3/2005 |
| EP | 1135322 | 4/2005 |
| EP | 1523054 | 4/2005 |
| EP | 1679111 | 7/2006 |
| EP | 0951529 | 8/2006 |
| EP | 1252678 | 11/2006 |
| EP | 1189678 | 7/2007 |
| EP | 1861610 | 12/2008 |
| EP | 1290747 | 2/2009 |
| EP | 1138096 | 10/2010 |
| EP | 2359928 | 8/2011 |
| EP | 2631213 A1 | 8/2013 |
| GB | 146110 | 11/1920 |
| GB | 669759 | 4/1952 |
| GB | 791946 | 3/1958 |
| GB | 820257 | 9/1959 |
| GB | 2432369 | 4/2010 |
| JP | 10052621 | 2/1998 |
| JP | 2003277019 | 10/2003 |
| JP | 2003282119 | 10/2003 |
| JP | 2007099528 | 4/2007 |
| JP | 2008171815 | 7/2008 |
| JP | 2008285404 | 11/2008 |
| TW | 200404739 | 4/2004 |
| TW | 200629635 | 8/2006 |
| TW | 2007040014 | 10/2007 |
| WO | 8806489 | 9/1988 |
| WO | 9919456 | 4/1999 |
| WO | 00022690 | 4/2000 |
| WO | 00056425 | 9/2000 |
| WO | 01008247 | 2/2001 |
| WO | 01012311 | 2/2001 |
| WO | 01012539 | 2/2001 |
| WO | 01026174 | 4/2001 |
| WO | 01050541 | 7/2001 |
| WO | 01050542 | 7/2001 |
| WO | 01068514 | 9/2001 |
| WO | 01070376 | 9/2001 |
| WO | 01073879 | 10/2001 |
| WO | 01093362 | 12/2001 |
| WO | 02038265 | 5/2002 |
| WO | 02049128 | 6/2002 |
| WO | 02069428 | 9/2002 |
| WO | 03002244 | 1/2003 |
| WO | 03026776 | 4/2003 |
| WO | 03077331 | 9/2003 |
| WO | 2003086964 | 10/2003 |
| WO | 2003089128 | 10/2003 |
| WO | 2003100900 | 12/2003 |
| WO | 2004038845 | 5/2004 |
| WO | 2004091005 | 10/2004 |
| WO | 2005001955 | 1/2005 |
| WO | 2005091785 | 10/2005 |
| WO | 2005119824 | 12/2005 |
| WO | 2006033773 | 3/2006 |
| WO | 2006049918 | 5/2006 |
| WO | 2006050335 | 5/2006 |
| WO | 2006133003 | 12/2006 |
| WO | 2007035467 | 3/2007 |
| WO | 2007037856 | 4/2007 |
| WO | 2008008279 | 1/2008 |
| WO | 2008033301 | 3/2008 |
| WO | WO2008/053080 A1 | 5/2008 |
| WO | 2009088962 | 7/2009 |
| WO | WO2010/004300 A1 | 1/2010 |
| WO | 2010033628 | 3/2010 |
| WO | 2010118221 | 10/2010 |
| WO | 2011059446 | 5/2011 |
| WO | 2012067612 | 5/2012 |
| WO | WO2013/158343 A1 | 10/2013 |
| WO | 2014099606 | 6/2014 |
| WO | WO2016/077496 A1 | 5/2016 |

OTHER PUBLICATIONS

Product literature and presentation entitled, "Innovations in Temporary Utilities Drive Game-Changing Cost Reductions for Upstream and Midstream Facilities", presented by Forrest Marsh of Aggreko, 21 pages, Sep. 2016, Houston, Texas.

"Analysis of Carbon Dioxide Reforming of Methane Via Thermodynamic Equilibrium Approach", by Tung Chun Yaw & Nor Aishah Saidina Amin, Jurnal Teknologi, Universiti Teknologi, pp. 31-49, Feb. 15, 2007, Malaysia.

Article entitled, "Steam reforming of methane, ethane, propane, butane, and natural gas over a rhodium-based catalyst", by Benjamin T. Schadel, Matthias Duisberg, and Olaf Deutschmann, Catalysis Today, 11 pages, published by Elsevier, Feb. 11, 2009, Germany.

Article entitled, "Syngas Production from Propane using Atmospheric Non-Thermal Plasma", by F. Ouni, A. Khacef, and J. M. Cormier, Gremi—Polytech Orleans, 12 pages, Feb. 23, 2009, France.

Article entitled, "Thermodynamic equilibrium analysis of combined carbon dioxide reforming with partial oxidation of methane to syngas", by Nor Aishah Saidina Amin and Tung Chun Yaw, International Journal of Hydrogen Energy, pp. 1789-1798, published by Elsevier, Feb. 5, 2007, Malaysia.

Article entitled, "High B.T.U. Gas", by Dr. Glenn C. Williams, Natural Gas, vol. 52, No. 7, pp. 575-576, Industrial and Engineering Chemistry, Jul. 1960, Cambridge, Massachusetts.

Novorocs Technologies LLC, Presentation entitled, "Flare Gas Recovery: An Alternative to Burning Profits", 18 pages, May 27, 2015, Rochester, New York.

Wartsila Corporation, "2015/2016 Wartsila Solutions for Marine and Oil & Gas Markets", pp. 1-206, Copyright 2015, Helsinki, Finland.

Notice of Allowance dated Sep. 10, 2010, issued in U.S. Pat. No. 7,866,161, entitled: "Method of Operating a Gas Engine Plant and Fuel Feeding System for a Gas Engine"; Issued Jan. 11, 2011; Inventors: Mahlanen et al.

International Search Report for International Application No. PCT/US2015/026,510; International Filing Date: Apr. 17, 2015; Applicant: Advanced Green Technologies, LLC; dated Sep. 18, 2015; 3 pages.

Written Opinion for International Application No. PCT/US2015/026,510; International Filing Date: Apr. 17, 2015; Applicant: Advanced Green Technologies, LLC; dated Sep. 18, 2015; 6 pages.

"Capstone Distributor BPC Engineering Installs First Two C1000s on Associated Gas in Russia", Capstone Turbine Corporation, 3 pages, May 31, 2011, Chatsworth, California.

"Capstone Continues Penetration of Russian Oil Fields With New Associated Gas Projects", Capstone Turbine Corporation, 3 pages, Feb. 6, 2012, Chatsworth, California.

"Capstone to Provide 1MW Microturbine to Kineticor Resource Corporation for Canadian Flare Gas Utilization", Capstone Turbine Corporation, 2 pages, Jul. 20, 2015, Chatsworth, California.

"Capstone Receives 4.6MW Order from Horizon Power Systems for Flare Gas Project", Capstone Turbine Corporation, 3 pages, Jan. 4, 2016, Chatsworth, California.

Gas Processing News, "Gas reformer improves methane number for offshore power generation", by R. Kaila and P. Jansson, 2013, 4 pages, Helsinki, Finland, Gulf Publishing Company.

Product literature from Austro Energy Systems Int. AG for the "Gas reformer AES3000", 24 pages, Vienna, Austria.

Wartsila Technical Journal Jan. 2013, "Converting low quality gas into a valuable power source", by Reetta Kaila and Peik Jansson, 5 pages, Jan. 2013.

PCI Precision Combustion, Inc. Presentation: "2013 Hannover Messe Group Exhibit Hydrogen + Fuel Cells", Apr. 11, 2013, Presenter: Anthony Anderson, Director, Marketing & Business Development, 23 pages, North Haven, Connecticut.

Elsevier, Chemical Engineering Research and Design 104, "Thermal design, modeling and validation of a steam-reforming reactor for fuel cell applications", by Marco Gianotti Pret; Domenico Ferrero; Andrea Lanzini; and Massimo Santarelli, pp. 503-512, 2015, Torino, Italy.

(56) References Cited

OTHER PUBLICATIONS

Doctoral Thesis of Margrete Hans Wesenberg, "Gas Heated Steam Reformer Modelling", 210 pages, Apr. 2006, Norwegian University of Science and Technology, Trondheim, Norway.
Journal of Power Sources, "A light hydrocarbon fuel processor producing high-purity hydrogen", by Daniel A. Loffler; Kyle Taylor; and Dylan Mason, IdaTech, LLC, 24 pages, Bend, Oregon.
TWENTYFOUR7, "Gas Reforming Creates Fuel From Waste", by Harriet Oster, pp. 43-45, Feb. 2013.

\* cited by examiner

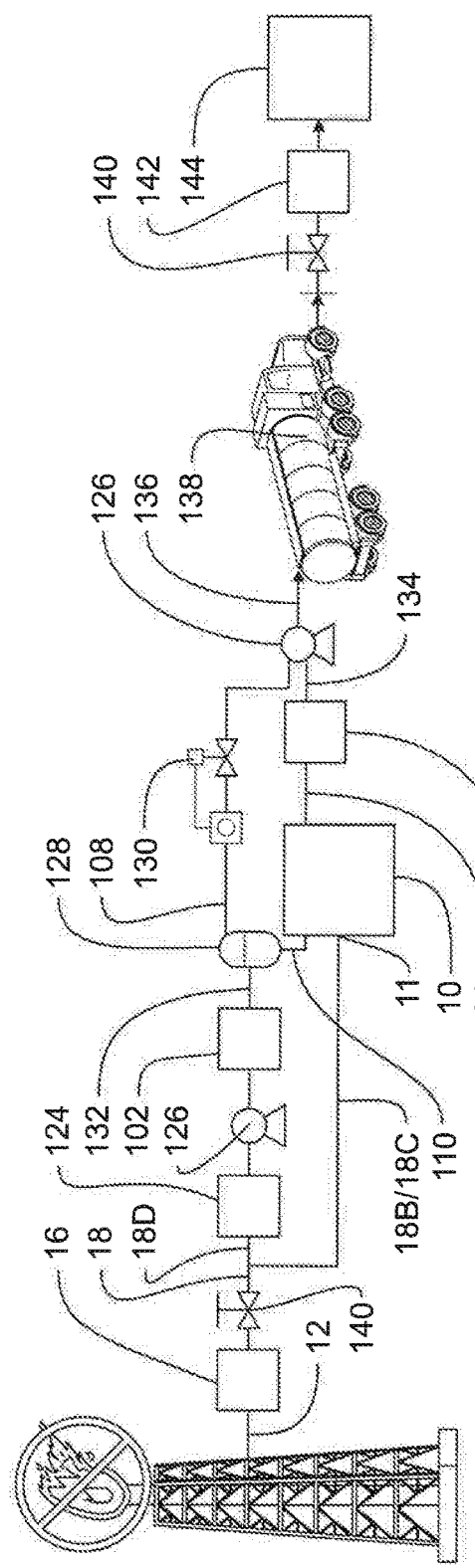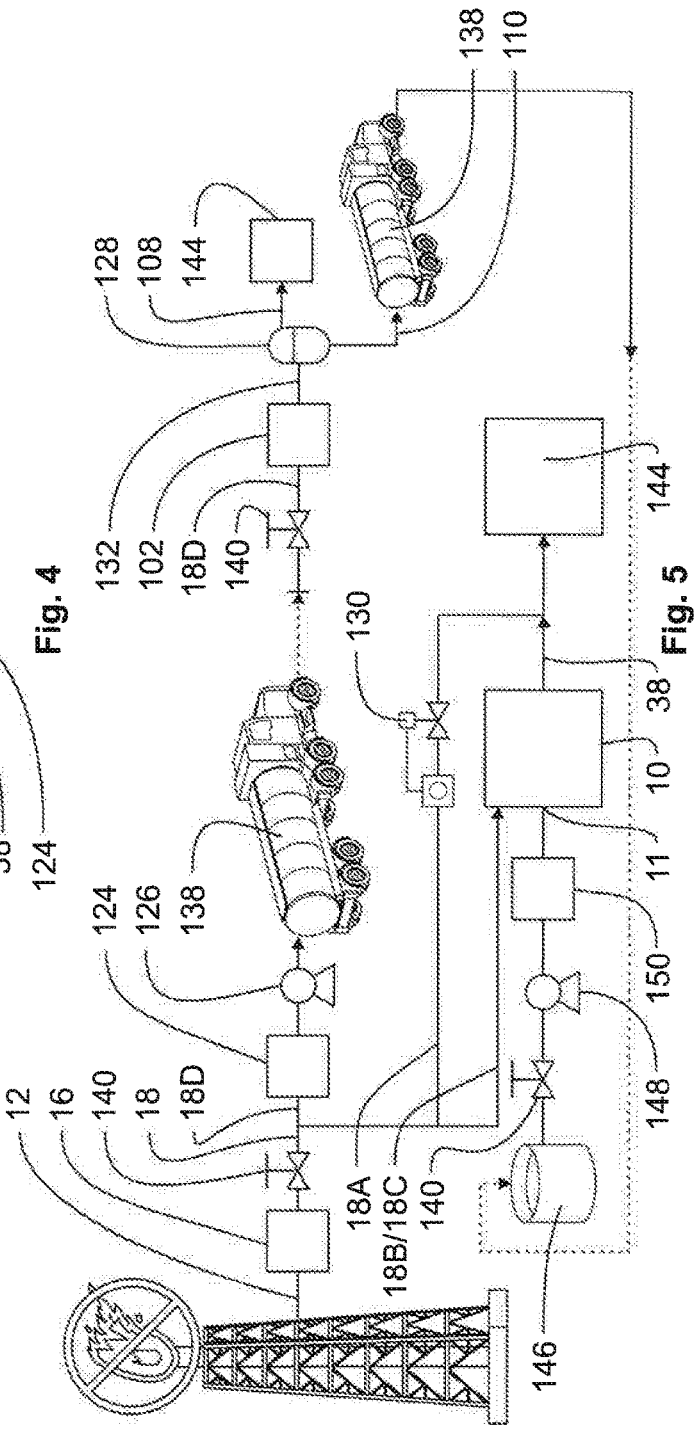

METHOD AND SYSTEM FOR CONVERTING ASSOCIATED GAS

CROSS-REFERENCE TO RELATED APPLICATIONS

This application claims priority to U.S. Provisional Patent Application No. 62/535,189, filed Jul. 20, 2017, the entire contents of which are hereby incorporated by reference.

TECHNICAL FIELD

The invention relates to a methods and apparatus for converting natural gas with heavier hydrocarbon gas content at remote locations to pipeline quality natural gas.

BACKGROUND

Oil wells often have an amount of natural gas associated (also referred to herein as "associated gas" and "flare gas") with them. Crude oil and natural gas are extracted from the oil wells together and the natural gas and crude oil must be separated. In remote areas with insufficient infrastructure or where the economics present a challenge, this associated gas may be flared. The flaring process causes carbon dioxide and volatile organic compound emissions and is being targeted for removal for environmental protection reasons.

Natural gas associated with oil wells can be high in alkanes other than methane (C1), such as ethane (C2), propane (C3) and butane (C4). These higher carbon number alkanes are of high caloric value and, in some embodiments, may allow for transport of the energy in the form of a highly dense liquid referred to as natural gas liquids ("NGLs").

Remote processing of natural gas to remove the "NGLs" or convert the entire stream to liquids has attracted great attention. The two leading processes in this industry are membrane separation and gas to liquid conversion. Both processes are energy intensive and typically require onsite electrical power generation.

Membrane separation pressurizes the stream to high pressures (1000+ PSI) and forces the gas through membrane sieves which force the liquids to condense and allow the liquids to be removed. Membrane separation is unable typically to remove ethane because its size is relatively close to methane. The resulting natural gas from membrane separation is not of pipeline quality because of its ethane content.

Gas to liquid conversion involves first converting the natural gas stream into synthesis gas, which is a combination of hydrogen, carbon monoxide, and carbon dioxide. The synthesis gas is then processed to convert the stream into high carbon number alkanes (e.g., by Fischer-Tropsch processes) which can be further refined into liquid products such as gasoline, diesel and methanol.

These two technologies are not well suited for removal and transport of natural gas streams at well sites, but are very energy intensive and require onsite electrical power to be utilized. Remote oil well sites have electrical demands that currently are fed by local diesel generators. Where the gas extracted from the oil well is of a high enough quality, natural gas generators ("genset") are used. Well sites prefer to use the gas from the nearby well because it is a byproduct of oil removal. Currently available and utilized natural gas generators require near pipeline quality natural gas in order to function optimally.

SUMMARY

The present invention is a system and a method to reform associated gas (also referred to herein as "Flare Gas") into synthesis gas by receiving a volume of Flare Gas, where the volume of Flare Gas includes a volume of methane (C1) and a volume of other alkanes (C2, C3, C4, etc.). The method can control both an inlet flow of the volume of Flare Gas and a volume of steam to at least one reformer system that will crack, convert, or change at least a portion of the volume of heavier (C2+) alkanes from the volume of Flare Gas. In this way, the at least one steam reformer system generates synthesis gas from the volume of Flare Gas and the volume of steam. The method may then further process the synthesis gas to convert it to a methane rich process gas which may be combined with Flare Gas to form an enriched product gas with a specific caloric value and methane number.

Embodiments of the present invention are advantageous in a number of respects:

A. Unit design: The system can convert non-methane hydrocarbon alkanes (C2+) of any composition, including 100% ethane and/or propane, to a methane rich process gas stream; and with carbon dioxide removal can produce a pipeline quality natural gas stream. System is modular, scalable and may be remotely monitored and controlled.

B. On-demand system: The system produces gas only as required/demanded by the applications—e.g., in case of genset, as genset load increases or decreases the system can increase or decrease gas production based on changes in at least one of several parameters (e.g., genset feed gas pressure and/or flow rate).

C. Steam reformer feed gas: The system proportionally produces, meters, and mixes saturated steam into the Flare Gas according to Flare Gas quality and application demand, and subsequently superheats the gas plus saturated steam mixture to a controlled temperature.

D. Process water recycle: A majority of process water (i.e., water/steam added to the Flare Gas) is condensed out, removed and recycled in the System; a controllable portion of water is allowed to slip into the methanation reactor (also referred to as a methanizer or SNG reactor).

E. Process water temperature control: Air to gas heat exchangers are used to control process water cooling.

F. Thermal management: recuperative heating/cooling is used throughout system to increase energy efficiency and unit control. Throughout the system input and output streams may be used for energy exchange.

G. System product gas control/enrichment: measurement of Flare Gas quality parameters including caloric value and/or Methane Number and/or composition can be used to control the steam to carbon ration ("S:C") of the reformer feed gas, component temperatures (e.g., super heater, reactors), and product gas quality ("Enrichment").

H. Purge system: automated start/stop generating and dispensing purge gas (nitrogen, argon, or other inert gases) system integrated to provide non-oxidizing inert gas blanket for startup, shut down as well as during downtime.

I. Catalyst life: monitor catalyst performance/life by monitoring reactor/catalyst thermal profile and/or midstream non-methane hydrocarbon composition.

J. Software/control: proportional control of S:C, product gas enrichment, burner management systems for reactors and super heater, safeguards, startup/shutdown, transient/upset/spike response, warning systems, smart systems for various system configurations and embodiments including, but not limited to, the fully integrated J-T adapted system (discussed below).

BRIEF DESCRIPTION OF THE DRAWINGS

The figure described below depicts various aspects of the methods, systems, and devices disclosed herein. It should be understood that each figure depicts an embodiment of a particular aspect of the disclosed methods, systems, and devices, and that each of the figures is intended to accord with a possible embodiment thereof. Further, wherever possible, the following description refers to the reference numerals included in the following figures, in which features depicted in multiple figures are designated with consistent reference numerals.

Non-limiting and non-exhaustive embodiments of the devices, systems, and methods, including the preferred embodiment, are described with reference to the various figures disclosed.

Figure 1A:
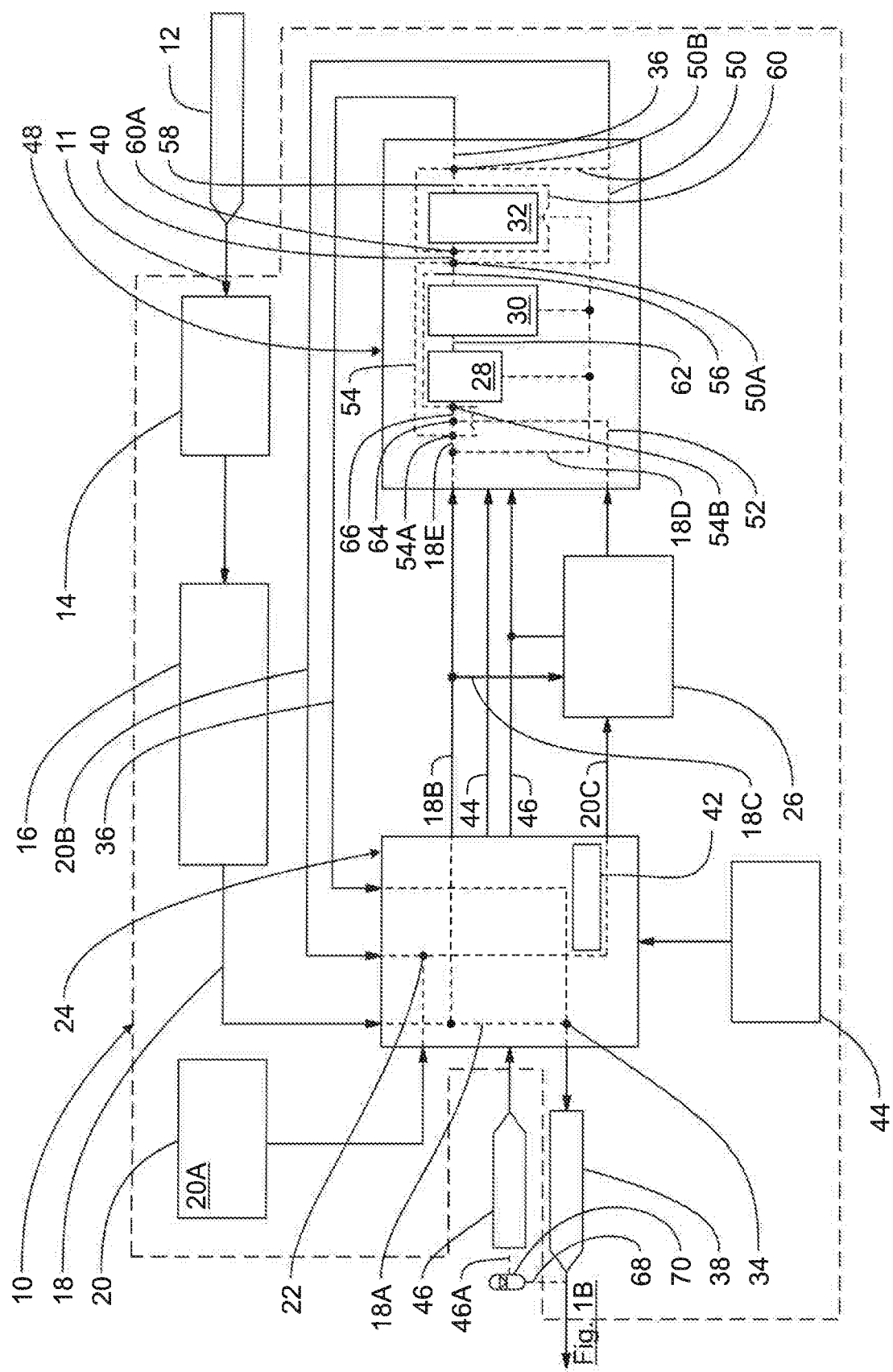

The headings provided herein are for convenience only and do not necessarily affect the scope or meaning of the claimed embodiments. Further, the drawings have not necessarily been drawn to scale. For example, the dimensions of some of the elements in the figures may be expanded or reduced to help improve the understanding of the embodiments. Moreover, while the disclosed technology is amenable to various modifications and alternative forms, specific embodiments have been shown by way of example in the drawings and are described in detail below. The intention, however, is not to limit the embodiments described. On the contrary, the embodiments are intended to cover all modifications, equivalents, and alternatives falling within the scope of the embodiments as defined by the appended claims.

Figure 1B:
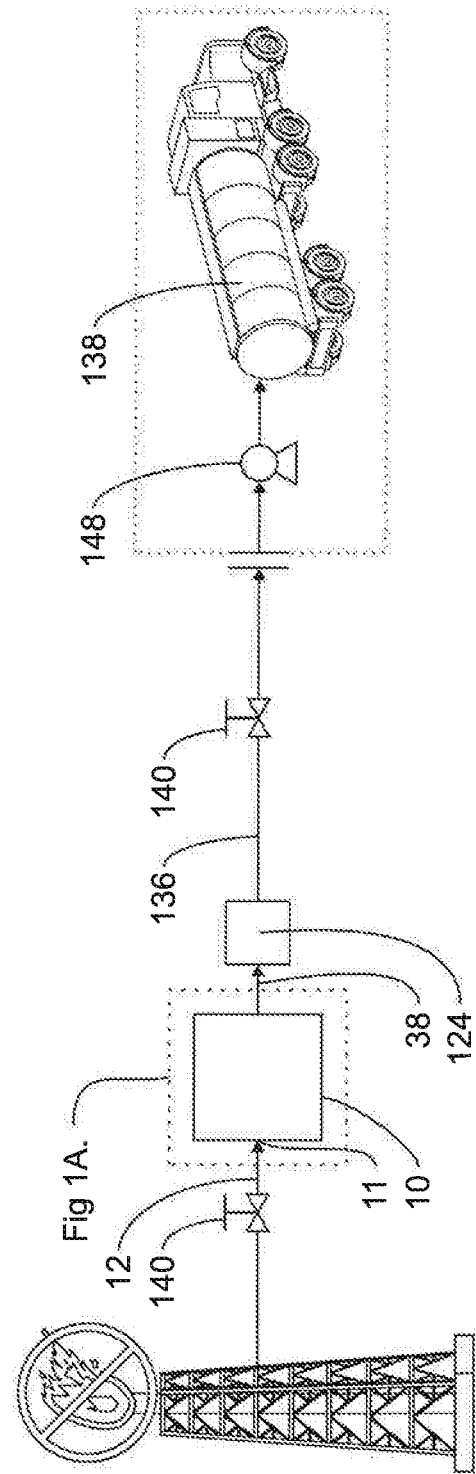
Figure 2:
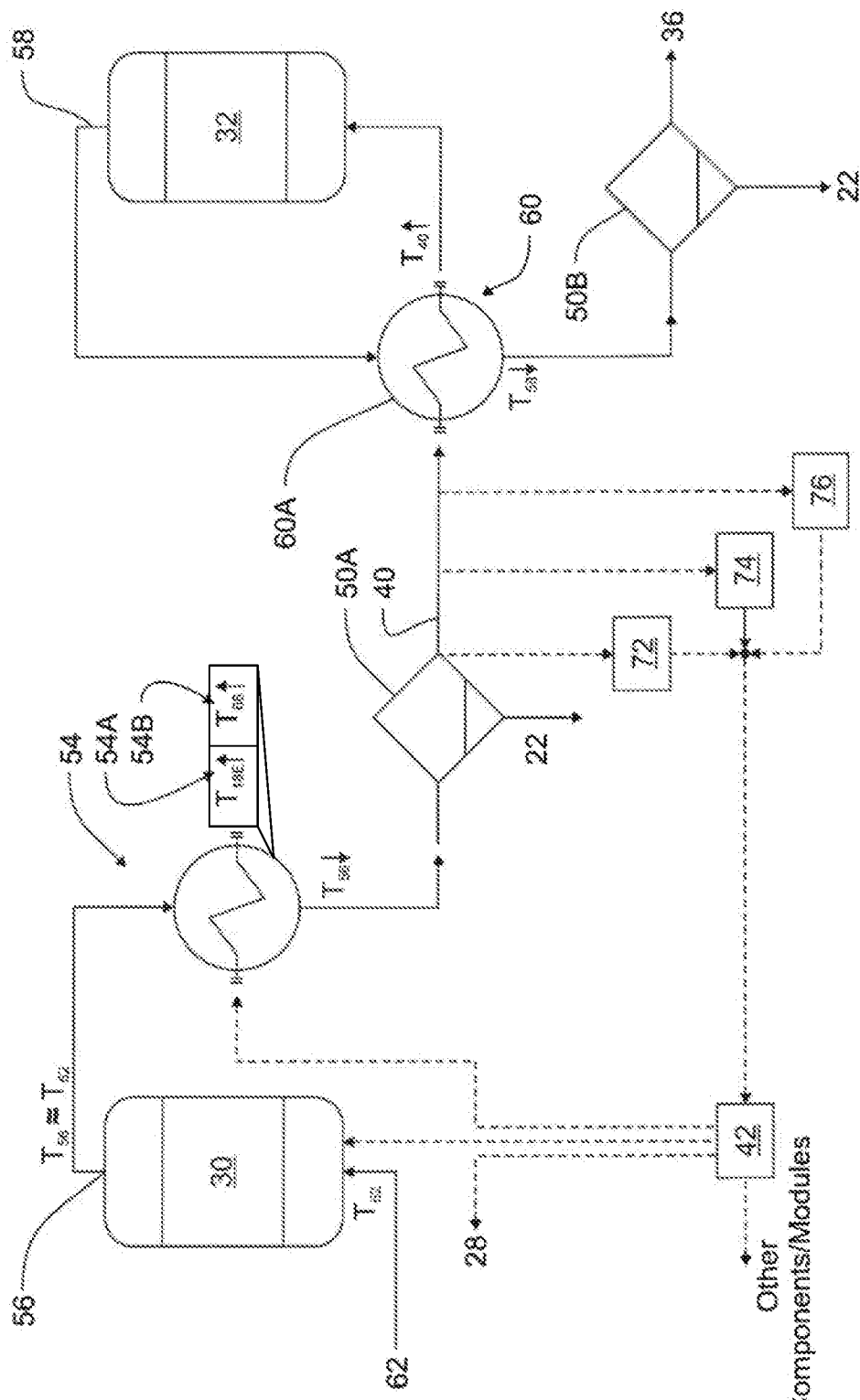
Figure 3:
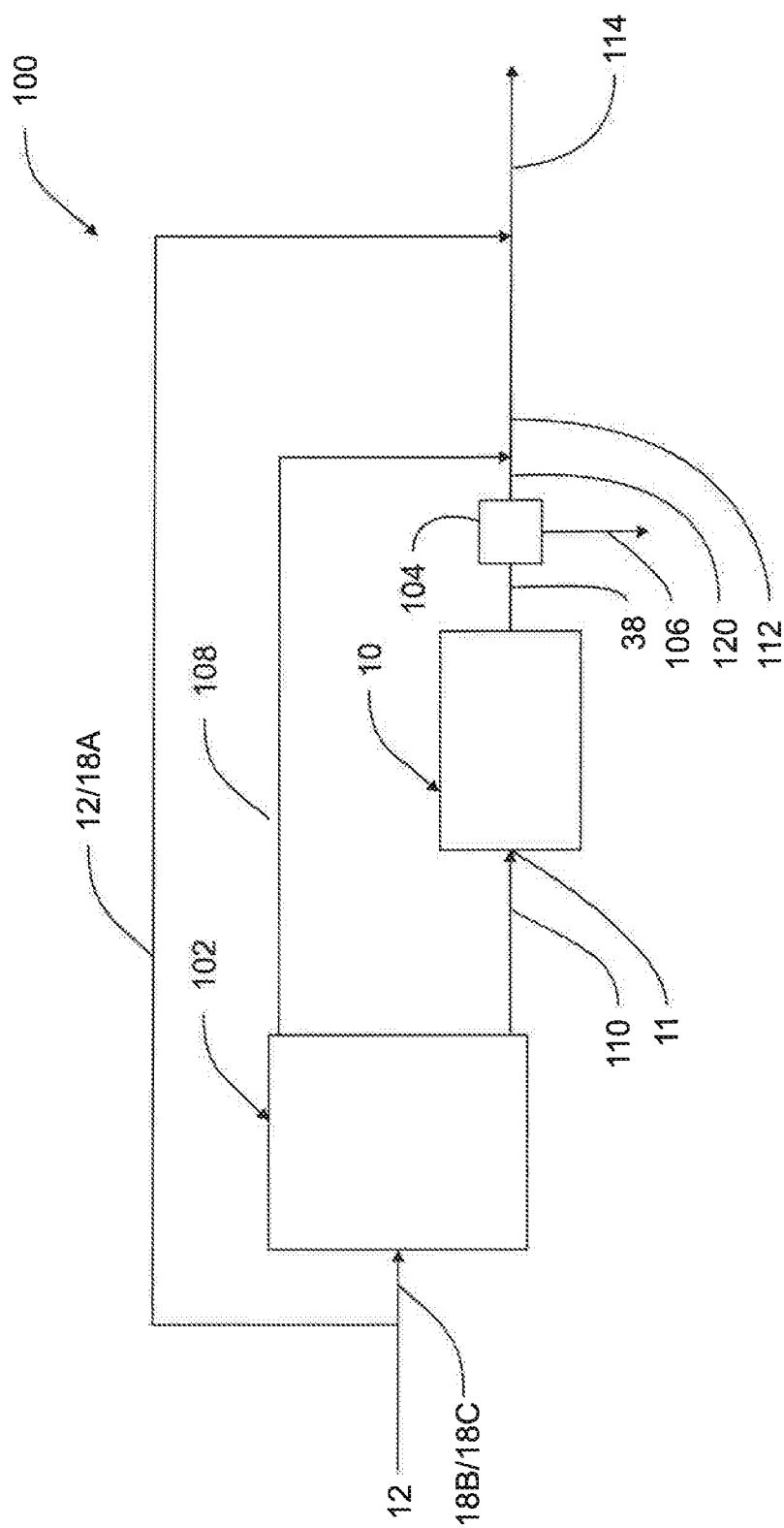

FIG. 1A illustrates various modules of one embodiment of a system for converting associate gas to a methane-rich gas stream;

FIG. 1B illustrates an additional aspect of the present invention for transporting the product gas off site;

FIG. 2 illustrates the interconnecting fluid circuits of the HHR and SNG, and the control logic schematic for HHR catalyst life monitoring and adjustment; and FIGS. 3-5 illustrate alternative embodiments of the present invention adapted with a Joule-Thomson apparatus.

DETAILED DESCRIPTION

Now turning to FIG. 1A, one embodiment of the present invention includes a modular associated gas conversion system 10 with independent components or assemblies or modules (also referred to herein as "skids") that are interconnected fluidly and/or electrically (such as power; measured data collection, analysis and transmission; control signals) to act as one unit to process associated gas stream 12 (also referred to herein as "flare gas" or "raw feed gas" or natural gas stream). System 10, with an associated gas stream input 11, is capable of being scaled or sized to an end-user's needs that may include, but is not limited to, a combination of a compressor skid 14 (as required), a sulfur removal system 16 (sized per wellsite), tank water 20A in water storage tank 20, a common skid 24, a purge system 44, a steam generator (or "boiler skid") 26, and a process skid 48. Common skid 24 can house controller 42 and the fluid and electrical interconnections with and between the other modules forming a closed loop control network to monitor, meter, and control gas flows (including feed gas, saturated and superheated steams), water flow, and electrical power distribution, as well as all other system parameters. Process skid 48 can include a super heater (S/H) 28, a heavy hydrocarbon reactor (HHR) 30, a synthetic natural gas generator (SNG) 32, a water removal/recovery system 50, and recuperative heating systems 54, 60. Each module will be discussed in detail below.

System 10 can convert non-methane hydrocarbon gases of any composition, including 100% ethane and 100% propane, to a methane rich gas stream. A carbon dioxide removal system can be added to system 10 if carbon dioxide levels in product gas 38 are too high to produce pipeline quality methane rich gas stream even after enrichment of processed gas 36 with system feed gas 18A (discussed in detail below).

System 10 can be remotely monitored and controlled to monitor all conditions within the system including quality of all gas streams (including transient/upset/spike responses), catalyst life, temperatures, pressures, flows, etc., such that safeguards are in place with warning systems and emergency shutdowns. System 10 can also be capable of remote starts.

In some embodiments, an associated gas stream 12, including alkane gases, may include a varying composition that enters system 10. Associated gas stream 12 may contain alkanes methane, propane, ethane, butane, pentane, hexane in high mole fractions as well as carbon dioxide, nitrogen, water vapor, and hydrogen sulfide.

In some embodiments where the well pressure is less than the System requirements, compressor skid 14 compresses the associated gas stream 12 to a defined gage pressure and transmits the associated gas stream 12 to system 10 in an on-demand configuration. Compressor 14 can be a single or multi stage well head gas compressor that compresses associated gas stream 12 into a pressure vessel (not shown), which holds the associated gas at a higher pressure than required by system 10. The compressor 14 has a set-able outlet pressure and is on-demand.

Sulfur removal system 16 can remove organic sulfurs and hydrogen sulfide from an associated gas stream 12 to create a sulfur free feed gas 18 (also referred to as "system feed gas"). In some embodiments, sulfur removing system 16 can remove the organic sulfurs and hydrogen sulfide through hydrogenation and absorption. Any commercially available sulfur removal system is acceptable.

Tank water 20A from water storage tank 20 and recovered water 20B (discussed above and further below) can be mixed at system water mixing point (valve or supply tank) 22 within common skid 24 to form system water 20C. The process can initially input tank water 20A from water storage tank 20 to charge system 10. Once system 10 is operational, recovered water 20B recovered within system 10 can supply 80-90% of system water 20C required by system 10. Therefore, only a small portion of system water 20C required by system 10 needs to be supplied by tank water 20A in water storage tank 20. However, system 10 is designed to operate with system water 20C being completely supplied (100%) by tank water 20A in water storage tank 20 when necessary. Tank water 20A stored in water storage tank 20 and recovered water 20B will be processed to remove dissolved solids and other contaminants and undesirable constituents. Any commercially available process is acceptable, including but not limited to, chemical (e.g., water softener), de-aeration, de-ionization, and filtering.

System water 20C is routed to steam generator 26 to produce steam 52 having conditions ranging from saturated to superheated. The temperature of tank water 20A from water storage tank 20 is at a variable ambient temperature between 0-45° C. The temperature of recovered water 20B will be higher than the water temperature of tank water 20A from water storage tank 20 due to recuperative heating within system 10, and is typically 60-65° C. (discussed in detail below). Since the temperature of system water 20C is higher than ambient, the required heating of system water 20C by steam generator 26 is reduced due to recuperative heating. Therefore, less energy is used to increase the water temperature of system water 20C to steam saturation temperature, and the steam generator and its burner life are extended due to less load.

According to demand and/or steam to carbon ratio System 10 produces, meters, mixes, or proportions steam 52 into system feed gas 18E to form feed gas 66 which is a proportioned mixture of steam and feed gas. One embodiment of the present invention has a constant steam to carbon ratio of 2.3, independent of system demand. Other S:C ratios are acceptable depending on operational parameters, such as S:C 6 during start up to generate excess hydrogen so the catalyst in the HHR 30 does not carbonize.

System feed gas 18 can pass through common skid 24. A portion 18A of the system feed gas 18 can be routed to an enrichment mixing valve 34 to blend with processed gas 36 in an amount equal to a predetermined or variable percent of processed gas 36 (enrichment percent, % E) to form product gas 38. The % E is set to yield and/or control certain targeted values for product gas 38 including, but not limited to, minimum Methane Number and maximum energy density. The enrichment percent can either be a predetermined constant or a variable set point changing with the properties of certain system gases including, but not limited to, feed gas 18 and processed gas 36. In addition, enrichment of system 10 processed gas 36 increases system 10 total product gas 38 capacity. In cases where % E is zero, processed gas 36 has the same gas composition as product gas 38, and the terms are interchangeable herein with regards to technical and legal interpretation. The remaining portion 18B of the system feed gas 18 exits common skid 24 for reforming. The predetermined enrichment percent (% E) can be determined based on measured heating value and/or Methane Number and/or composition of the system feed gas 18 (or associated gas stream 12), processed gas 36 and/or product gas 38. The % E, in combination with other process controls, can be used to control S:C ratios and component temperatures to adjust the methane percentage in the product gas 38. In other words, the predetermined percentage is based on one or more of measurement of heating value, Methane Number and composition of feed gas, processed gas, and/or product gas. One embodiment of the enrichment (or blending) strategy includes a Flame Ionization Detector (FID) and an Infrared composition sensor to control and/or maintain the % E at its predetermined value by measuring the heating value of various system 10 gas streams. The enrichment percent determination can be automated to vary the enrichment percentage based on real-time fluctuations in constituent compositions of certain system 10 gas streams such as system feed gas 18 (or associated gas stream 12). An infrared composition sensor (not shown) in concert with the FID can result in higher reliability in detecting changes in non-methane hydrocarbons (NMHC) which yield variations in gas heating value. Oxygen sensors in burners can further aid with energy content calculations to facilitate higher confidence in the analyses needed for secure control of % E and other system 10 parameters. For example, a Flame Ionization Detector (FID) can use HHR dry reformate 40 as a reference flame (see FIG. 2) to measure the ionization extent of system feed gas 18. The dry reformate composition is relatively stable independent of system feed gas 18 (or associated gas stream 12) composition. FID determined ionization values in combination with IR sensor determined composition measurements could be compared for system gases including, but not limited to, feed gas 18, associated gas stream 12, processed gas 36, and product gas 38 to control system parameters such as S:C, operating temperatures, and the constant or variable enrichment percent. These measurements, analysis, and adjustments are performed by controller 42, which is in electrical connectivity with all of the modules to receive, store, and analyze measured parameters and to transmit control commands to the modules to adjust flow meters, valves, burner temperature settings, etc. to optimize the product gas 38. Enrichment reduces the load on system 10 or, alternatively, increases system 10 capacity as well as dilutes CO2 and inert gases in processed gas 36.

A portion 18C of system feed gas 18B can be routed to fuel the burner of steam generator 26. Another portion 18D of system feed gas 18B can be routed to fuel the burners of super heater 28, HHR 30, and SNG 32. The remaining portion 18E of the system feed gas 18B can be routed through super heater 28 to increase the temperature of system feed gas 18E up to or about the Equilibrium Temperature of HHR 30, thereby operating HHR 30 in Thermodynamic Equilibrium, where HHR inlet gas temperature T62 substantially equals HHR outlet gas temperature T56 (see FIG. 2). Though the HHR 30 can be an isothermal reactor, as discussed above, it can also be an adiabatic reactor.

Purge system 44 can be fluidly connected to HHR 30 and SNG 32 for use during startup, shutdown, or heat ups (such as when the reactor temperature is less than 200° C.) to purge hydrocarbons from HHR 30 and SNG 32 to protect the catalyst from formation of nickel carbonyl by displacing flammable gases. Purge system 44 can include one or both of a gas generator and high-pressure gas storage tanks. Purge system 44 can be manually operated and/or automated to dispense purge gas into HHR 30 and SNG 32 to provide a non-oxidizing environment for the catalyst. The purge system 44 can also be fluidly connected to water removal/recovery system 50 for de-aeration of recovered water 20B, which can reduce the use of oxygen scavenging chemicals. Purge system 44 can be used during non-operation, startup, shutdown, and heat ups to purge hydrocarbons and any oxidizing agents from the one or more of the heavy hydrocarbon reactor and the synthetic natural gas generator to provide an inert gas blanket over the catalyst to prevent or mitigate oxidation from exposure to air and formation of nickel carbonyl by displacing flammable gases. High purity inert gases such as nitrogen and argon are acceptable.

System 10 can create pipeline quality natural gas from associated gas stream 12 to generate Power 46 for operation of on-site equipment and off-site utilities during system 10 operation. On site power may be fueled by portion 68 of product gas 38. Power 46 can be supplied to each module requiring electricity, such as the controller 42, burners in the steam generator 26, super heater 28, HHR 30, and SNG 32. Accumulator 70 can be in-line with Power 46 to store product gas portion 68 for startup fuel, for reserve fuel when there is a fluctuation in (transient flow) or interruption of associated gas stream 12, and for reserve fuel for other causes of inoperability of system 10 for producing product gas 38.

FIG. 1B is an illustration of how the product gas 38 produced from the gas conversion system 10 discussed in detail in FIG. 1A is prepared for transportation to another site. Product gas 38 can flow through dehydrator 124 to remove liquids from product gas 38 to form a substantially dry blended high methane rich product gas 136 suitable for compression. The substantially dry blended high methane rich product gas 136 can be metered through valve 140 for controlled pumping by pump 148 into a transportation container, such a tanker truck 138, for delivery to another location where substantially dry blended high methane rich product gas 136 can be used as fuel for power generation units, such as gensets.

Now turning to FIGS. 1A and 2, illustrating recuperative heating systems 54 and 60 in accordance with one embodiment of the present invention will now be described. System power requirements have been reduced to operate, for example, the burners of super heater 28 and SNG 32 with the use of recuperative heating systems 54, 60. Recuperative energy transfer system 54 is comprised of two heat exchangers, 54A and 54B designed to perform a first heating step by heat exchanger 54A to increase the temperature of system feed gas 18B prior to mixing it with saturated steam 52 at mixing valve 64, forming feed gas 66 which is a proportioned mixture of steam and feed gas 18B, and then perform a second heating step by heat exchanger 54B to increase the temperature of feed gas 66 prior to entry into super heater 28, which forms feed gas 62 which is superheated feed gas 66. HHR 30 can receive feed gas 62 onto leading edge of catalyst to crack at least a portion of the non-methane hydrocarbons into carbon oxides and hydrogen to form a midstream gas (as referred to as HHR wet reformate 56) containing the feed gas methane, the carbon oxides, and the hydrogen. The HHR wet reformate 56 can be routed to heat exchanger 54B to transfer a portion of its heat energy to feed gas 66, thereby reducing the temperature of HHR wet reformate 56 and increasing the temperature of feed gas 66. Reduced temperature HHR wet reformate 56 is then routed to heat exchanger 54A to transfer a second portion of its heat to system feed gas 18E, thereby further reducing the temperature of HHR wet reformate 56 and increasing the temperature of system feed gas 18E. The reduced temperature of HHR wet reformate 56 exiting recuperating energy transfer system 54 is prepared for water removal by water removal/recovery system 50 (discussed in detail below). The temperature of recovered water 20B is still above water boiling point temperature after being used in the recuperative energy transfer system 54 to increase the temperature of feed gas 66 and HHR dry reformate 40. Thereby making the temperature of the system water 20C being higher than the water boiling point temperature prior to entry of the system water 20C into the steam generator 26. It should be understood that heat exchanger 54A and heat exchanger 54B can include one or more heat exchangers of any suitable construction and type.

Recuperative energy transfer system 60 is designed to increase the temperature of HHR dry reformate 40 at heat exchanger 60A prior to entry into SNG 32, where at least of portion of the carbon oxides and the hydrogen is converted into reformed methane to form the processed gas 36. SNG reformate gas 58 can be routed to SNG heat exchanger 60A to transfer a portion of its heat to HHR dry reformate 40, thereby reducing the temperature of SNG reformate gas 58 and increasing the temperature of HHR dry reformate 40. The reduced temperature of SNG reformate gas 58 exiting recuperative energy transfer system 60 is prepared for water removal by water removal/recovery system 50 (discussed in detail below). It should be understood that heat exchanger 600A can include one or more heat exchangers of any suitable construction and type.

In summary, recuperating energy transfer systems 54 and 60 reduce the load on the burner management systems of Super Heater 28, HHR 30, and SNG 32, thereby reducing burner gas consumption, system emissions, and extending catalyst life due to consistent desired reactor feed gas temperatures and lower temperature gradients within HHR 30 and SNG 32.

Use of tank water 20A in water storage 20 has been reduced during operation of system 10 because water removal/recovery system 50 removes water from the gas stream at two stages: between HHR 30 and SNG 32 (hereinafter referred to as "midstream water removal" 50A), and between SNG 32 and enrichment mixing valve 34 (hereinafter referred to as "processed gas water removal" 50B). Midstream water removal 50A and processed gas water removal 50B can include one or more heat exchangers, dryers, water knockouts, and/or coalescing and membrane filtration. HHR dry reformate 40 is formed when water vapor is removed from HHR wet reformate 56. SNG dry processed gas 36 (also referred to herein as "processed gas") is formed when water vapor is removed from SNG wet processed gas 58. Midstream water removal 50A and processed gas water removal 50B are each capable of removing 0-100% of the water from the midstream gas and processed gas 36, respectfully. The recovered water is used to replenish at least a portion of the system water consumed during chemical reactions within at least one of the heavy hydrocarbon reactor and the synthetic natural gas generator. In summary, midstream water removal 50A removes water vapor from the midstream gas (or HHR wet reformate 56) to form a first removed water portion and supplies a first removed water portion to the system water mixing point 22, and processed gas water removal 50B removes water vapor from the processed gas 36 to form a second removed water portion and supplies the second removed water portion to the system water mixing point 22. Total water recovery can be about 90%. System 10 is designed to vary the amount of recovered water 20B from 0% to about 90%.

Midstream water removal 50A can allow a portion of water vapor in HHR wet reformate 56 to "slip" into the SNG reactor by controlling the cooling (more cooling, less slip) of HHR wet reformate 56 such that HHR dry reformate 40 contains a predetermined percentage of water vapor. In the event of HHR catalyst degradation and/or high process gas flows, non-methane alkane species can slip to SNG 32. This introduction of non-methane alkanes into SNG 32 is undesirable due to the potential for catalyst coking. Coking is caused by hydrocarbon cracking on the hot catalyst active sites without the presence of water. SNG catalyst coking can be mitigated by slipping water vapor to SNG 32 to react with the non-methane hydrocarbons. Midstream water removal 50A, upon detection of non-methane hydrocarbons above a predetermined threshold in the midstream gas, is capable of removing less than 100% of the water vapor from the midstream gas to provide sufficient water vapor within the SNG 32 to reduce or prevent catalyst damage. The amount of water vapor slip is controlled by adjusting the water knockout temperature using active/variable heat exchangers. One example of variable heat exchange can be implemented by by-passing one or more heat exchangers which are connected in series or parallel. Another example of variable heat exchange can be implemented by controlling the air mass flow across one or more air-to-gas heat exchangers where the air is pulled from the ambient environment and the gas is the process gas stream. This control of water vapor slip can be used to extend the life of the HHR catalyst, as well as SNG catalyst, in conjunction with or instead of other extension methods, such as raising HHR 30 temperature (discussed in detail below).

Catalyst life in HHR 30 and SNG 32 can be monitored for performance and life degradation by monitoring reactor/catalyst temperature profile and/or non-methane hydrocarbon composition of HHR and/or SNG reformates. Arrays of thermocouples can line the interior of HHR 30 and/or SNG 32 to create a real-time temperature profile that can identify contaminated, deteriorated, or otherwise compromised catalyst.

Also, non-methane hydrocarbon composition in the gases 56 and 58 exiting HHR 30 and/or SNG 32 can also be determinative of deteriorated catalyst. Now turning to FIG. 2 for an illustration of one embodiment that measures non-methane hydrocarbon composition in HHR wet reformate 56 exiting HHR 30. Measurements from thermocouple 72 in midstream water knock-out 50A and from non-methane hydrocarbon detector 74 downstream of midstream water knock-out 50A can be used to determine if the temperature within HHR 30 should be increased to off-set the loss of performance of the deteriorated catalyst with more performance from the remaining catalyst, thereby increasing the reforming capability of the remaining catalyst such that non-methane hydrocarbon slippage from HHR 30 is reduced back to acceptable limits. As shown in FIG. 2, the burner of HHR 30 can be signaled to increase the temperature within HHR 30. An alternative is to increase the outlet temperature 162 of Super Heater 28 by increasing the temperature within Super Heater 28. Further, simultaneously increasing the outlet temperature 162 of Super Heater 28 and increasing burner temperature of HHR 30 may be desirable. Variable heat exchangers, such as those in recuperative heating system 54, can be adjusted accordingly to remove excess heat from HHR wet reformate 56 as needed.

System 10 can operate as an on-demand system to produce processed gas 36 only as required or demanded by the applications—e.g., in case of genset, as genset ramps up, system 10 can increase steam and feed gas 18B flow to meet the ramping genset feed gas need/demand; and vice versa with system 10 ramping down in concert with genset demand to point of shutoff. System 10 is capable of either matching the genset demand by controlling steam flow with feed gas 18B flow following (18B metered in proportion to steam flow) or matching genset demand by controlling feed gas 18B flow with steam flow following (steam metered in proportion to feed gas 18B flow). The water flow of course follows steam demand. Below are examples of On-Demand based control of system 10 for monitoring and controlling production of product gas 38 in real time:

One embodiment of the present invention combines steam reforming technology with automated direct feedback control to match the feed gas consumption rate of the supported application, such as a generator, gas compression engine, or any other gas consuming unit with the product gas 38 production rate of system 10. System 10 can use pressure transducer(s) or sensor(s) as the feedback mechanism. Pressure at the application inlet 46A is used to determine whether the generator is shutdown, shutting down, starting up, or transiting between low and high power settings and visa-versa. This measured pressure value is fed into a closed loop control system to adjust the system 10 parameters to create the desired product gas 38 production rate.

Another embodiment of the present invention combines steam reforming technology with automated direct feedback control to match the feed gas consumption rate of the supported application, such as a generator, gas compression engine, or other gas consuming unit with the product gas 38 production rate of system 10. System 10 can use gas flow meters(s) as the feedback mechanism. Gas flow at the application inlet 46A is used to determine the required/desired production rate in real time. This production rate value is fed into a closed loop control system to adjust the feed gas 18B flow rate (in the case of steam flow following feed gas 18B flow) to create the required product gas 38 production rate.

Yet another embodiment of the present invention combines steam reforming technology along with automated direct feedback control to match the feed gas consumption rate of the supported application, such as a generator, a gas compression engine, or other gas consuming unit with the product gas 38 production rate of system 10. System 10 can use pressure transducer(s) or sensor(s) as the feedback mechanism. Pressure at the application inlet 46A is used to determine the required production rate in real time. This requirement is fed into a closed loop control system to adjust the steam flow rate (in the case of feed gas 18B flow following steam flow) to create the required product gas 38 production rate.

Yet another embodiment of the present invention combines steam reforming technology along with automated direct feedback control to match the feed gas consumption rate of the supported application, such as a generator, gas compression engine, or other gas consuming unit with the product gas 38 production rate of system 10. The system uses gas flow meters(s) as the feedback mechanism. Gas flow at the application inlet 46A is used to determine the required production rate in real time. This requirement is fed into a closed loop control system to adjust the steam flow rate (in the case of feed gas 18B following steam flow) to create the required product gas 38 production rate.

Examples illustrating various ways to adjust system parameters include:

1. Increase flow of the steam of the steam generator in response to a decrease in pressure from the pressure sensor below a minimum pressure threshold when the one or more power generation units are ramping up to meet increased power demand.

2. Decrease pressure of system water in response to increased flow of the steam of the steam generator.

3. Decrease flow of the steam of the steam generator in response to an increase in pressure from the pressure sensor above a maximum pressure threshold when the one or more power generation units are ramping down to meet decreased power demand.

4. Decrease flow of the system water in response to maintain pressure in the system water.

5. Reduce flow of the steam and the associated gas 12 stream in response to the one or more power generation units shutting down.

6. Stop flow of system water in response to reaching a predetermined pressure target in the system water.

7. Increase flow of the steam and the feed gas 18B in response to the one or more power generation units ramping up for an increase in power demand.

8. Increase flow of the steam in response to increased flow of the feed gas

9. Increase flow of system water in response to increased flow of the superheated steam of the super heater.

10. Decrease flow of the feed gas in response to the one or more power generation units ramping down for a decrease in power demand.

11. Decrease flow of the steam in response to decreased flow of the feed gas.

12. Decrease flow of system water in response to decreased flow of the superheated steam of the super heater.

Stop flow of the feed gas in response to the one or more power generation units shutting down in response to no power demand.

14. Stop flow of the steam in response to zero flow of the feed gas

15. Stop flow of system water in response to zero flow of the steam.

16. Adjust the steam flow rate to increase the pressure at the inlet of the one or more power generation units back to the target pressure level, thereby creating the required product gas production rate.

17. Adjust steam flow rate to create the required product gas production rate.

18. Adjust feed gas flow rate to a predetermined steam to carbon ratio for any required product gas production rate.

19. Adjust the steam flow based on a predetermined steam to carbon ratio as feed gas increases to maintain a target pressure at the inlet of the one or more power generation units.

20. Adjust the feed gas flow based on a predetermined steam to carbon ratio as the steam flow increases to maintain a target pressure at the inlet of the one or more power generation units.

In accordance with various embodiments, the system 10 includes one of more gas flow meters disposed in the system 10, wherein gas flow at an inlet is a feedback mechanism to adjust feed gas flow rate to create the required product gas production rate.

FIG. 3 illustrates alternative embodiments of the present invention including a gas conversion system 10 (discussed in detail in FIG. 1A) adapted with a fully integrated Joule-Thomson (J-T) apparatus 102 (J-T adapted system). The Joule-Thomson apparatus 102 can be a commercially available or custom designed system that facilitates the Joule-Thomson effect and is fully integrated with system 10 and related systems such as software and controls as well as various system 10 processes which may include synthesis and thermal management loops. As such, the J-T adapted system functions as a single gas conversion system which receives feed gas 12 and converts it to a methane rich product gas 112 which can be enriched with a portion of feed gas 12 to adjust certain gas properties including, but not limited to, methane number and BTU value, in the form of product gas 114. The J-T adapted system increases system production capacity and improves product gas quality by splitting feed gas 12 into a first methane rich gas stream and a primarily NGL gas stream wherein the NGL gas stream is processed by system 10 into a second methane rich gas stream and combined with the first methane rich gas stream to produce product gas 112 which may be enriched with a portion of feed gas 12. The integrated J-T apparatus 102 is in fluid communication with associated gas inlet 11 of the gas conversion system 10. Generally, J-T apparatus 102 is capable of receiving the feed gas 12 to separate the feed gas 12 into (a) a J-T liquid 110 containing primarily non-methane hydrocarbons (C2, C3, C4+) also referred to as NGLs, wherein the J-T liquid 110 in gaseous form is supplied to system 10 as feed gas 11, and (b) a J-T gas 108 containing primarily methane and lessor amounts of non-methane hydrocarbons (C2, C3), wherein the J-T gas 108 is blended with the product gas 38 or the product gas 120 to form product gas 112.

Associated gas stream 12 can be split into two streams: a blend or bypass stream of sulfur free natural gas stream 18A, and a sulfur free natural gas stream for J-T apparatus 102 feed gas 18B. The details of the present system 10 are discussed in detail above. The Joule-Thomson apparatus 102 facilitates the Joule-Thomson effect, whereby the sulfur free natural gas stream for system feed gas 18B is separated into two streams: a J-T gas stream 108 that contains primarily methane and lessor amounts of non-methane hydrocarbons (C2, C3), and a J-T liquid stream 110 that contains primarily non-methane hydrocarbons (C2, C3, C4+) also referred to as NGLs. The J-T liquid stream is vaporized prior to entering the gas conversion system 10, which produces the product gas 38 (discussed in detail above). One embodiment of the product gas 38 can include methane content in the range of 80-90%, carbon dioxide content in the range of 10-15%, and hydrogen content about 1%. Product gas 38 may be passed through a carbon dioxide removal apparatus 104 to substantially remove carbon dioxide 106 to form a higher methane content product gas 120. J-T gas stream 108 can be blended with product gas 38 or product gas 120 in an amount equal to a predetermined blend percent of product gas 38 or product gas 120, up to 100% of J-T gas stream 108 produced, to expand system 10 production capacity and improve product gas quality including, but not limited to, adjusting for the desired methane number and/or gas BTU value in the form of a first blended product gas 112. Then the bypass stream of sulfur free natural gas stream 18A can be blended with the first blended product gas 112 in an amount equal to a predetermined enrichment percent of the first blended product gas 112 to expand production capacity of the J-T adapted system and improve product gas quality including, but not limited to, adjusting for the desired methane number and/or gas BTU value in the form of a second blended product gas 114.

The J-T adapted system can operate as an on-demand system to produce second blended product gas 114 only as required or demanded by the applications—e.g., in case of genset, as genset ramps up, J-T adapted system will increase J-T apparatus feed gas 18B flow and natural gas stream 18A flow to meet the ramping genset feed gas need/demand; and vice versa with J-T adapted system ramping down in concert with genset demand to point of shutoff. J-T adapted system is capable of either matching the genset demand by controlling feed gas 18B flow and having natural gas stream 18A follow with 18A flow equal to a pre-determined percent of product gas 114 flow (enrichment target), or by controlling natural gas stream 18A flow and having feed gas 18B follow with 18B flow adjustment occurring only when 18A flow represents an enrichment percent exceeding pre-set upper or lower enrichment percent limits. When feed gas 18B flow adjustment is necessary, 18B flow will increase or decrease according to an algorithm determined amount to return natural gas stream 18A to the enrichment target. Below outlines an example of on-demand based control of J-T adapted system for monitoring and controlling production of product gas 114 in real time An embodiment of the present invention combines the J-T adapted system with automated direct feedback control to match the feed gas consumption rate of the supported application, such as a generator, gas compression engine, or other gas consuming unit with the product gas 114 production rate of the J-T adapted system. J-T adapted system can use pressure transducer(s), pressure sensor(s) or gas flow meters as the feedback mechanism. Pressure or gas flow at the application inlet 46A is used to determine whether the generator is shutdown, shutting down, starting up, or transiting between low and high power settings and visa-versa. This measured pressure or gas flow is fed into a closed loop control system to adjust the J-T adapted system parameters to create the required product gas 114 production rate.

Now turning to FIG. 4 illustrating yet another application of the J-T adapted system. Associated gas 12 passes through sulfur removal system 16 to form sulfur free natural gas stream 18, of which a portion 18C can be used as fuel for the burners of the gas conversion system 10 and the remaining portion 18D is feed gas for the J-T apparatus 102. The J-T apparatus feed gas 18D can pass through a dehydrator 124 to reduce the liquid content and a compressor 126 to increase the pressure of the J-T apparatus feed gas 18D to suitable conditions for the J-T apparatus 102 to facilitate the J-T effect on the J-T apparatus feed gas 18D to form J-T processed feed gas 132. The J-T processed feed gas 132 is prepared for separation in the natural gas liquid separator 128 for separation into two streams: a J-T gas stream 108 that contains primarily methane and lessor amounts of non-methane hydrocarbons (C2, C3), and a J-T liquid stream 110 that contains primarily non-methane hydrocarbons (C2, C3, C4+). The J-T gas stream 108 can flow through main flow control 130 for regulation of flow to downstream compressor 126. J-T liquid stream 110, which is vaporized prior to entry into gas conversion system 10, is reformed in gas conversion system 10 to product gas 38. Product gas 38 flows through dehydrator 124 to reduce the liquid content to a substantially dry methane rich product gas 134 suitable for compression. J-T gas stream 108 and substantially dry methane rich product gas 134 flow through compressor 126 to adjust for the desired methane number and BTU value and to increase the pressure of the substantially dry blended methane rich product gas 136 suitable for filling a transportation container, such as a tanker truck 138. The tanker truck 38 can then be driven to a remote location and connected to valve 140 to regulate flow into the expander 142 to fuel a remote genset.

FIG. 5 illustrates another application of the gas conversion system 10 (discussed in detail in FIG. 1A) employing the J-T apparatus 102. However, in this embodiment, the J-T apparatus 102 is provided at a remote location. Associated gas 12 passes through sulfur removal system 16 to form sulfur free natural gas stream 18, of which a portion 18C can be used as fuel for the burners of the gas conversion system 10 and the remaining portion 18D is feed gas for the J-T apparatus 102 at the remote location. The J-T apparatus feed gas 18D can pass through a dehydrator 124 to reduce the liquid content and a compressor 126 to increase the pressure of the J-T apparatus feed gas 18D to suitable conditions for filling a transportation container, such as a tanker truck 138. The tanker truck 38 can then be driven to a remote location and connected to valve 140 to regulate flow into the J-T apparatus 102. The J-T apparatus feed gas 18D in the tanker truck 138 is at a pressure sufficient to facilitate the J-T effect on the J-T apparatus feed gas 18D to form J-T processed feed gas 132. The J-T processed feed gas 132 is prepared for separation in the natural gas liquid separator 128 for separation into two streams: a J-T gas stream 108 that contains primarily methane and lessor amounts of non-methane hydrocarbons (C2, C3), and a J-T liquid stream 110 that contains primarily non-methane hydrocarbons (C2, C3, C4+). The J-T gas stream 108 has sufficient methane and BTU value to be used as a fuel for the remote genset 144. The J-T liquid stream 110 is pumped into another tanker truck to deliver the J-T liquid stream 110 to a natural gas liquid tank 146 at another location for use as feed gas to a gas conversion system 10. The J-T liquid stream 110 in the natural gas liquid tank 146 is regulated through a valve 140 to a pump 148 where it is fed to a vaporizer 150 and subsequently to system 10 where it is reformed into a methane rich product gas 38. Sulfur free natural gas stream 18A can be blended with product gas 38 to adjust for targeted properties such as methane number and BTU value to produce an enhanced product gas for various local and remote uses including power generation and compression.

In summary, what has been described in a gas conversion system to form a product gas from an associated gas stream, wherein the associated gas stream contains methane and non-methane hydrocarbons. In one embodiment, the gas conversion system includes: a steam generator capable of receiving system water and outputting steam; a mixing valve system capable of flow controlling at least a portion of the associated gas stream and the steam, and outputting a feed gas which is a mixture of the steam and the at least a portion of the associated gas stream; a super heater capable of receiving the feed gas and superheating the feed gas to a predetermined temperature range to form a superheated feed gas; a heavy hydrocarbon reactor containing a first catalyst having a leading edge and capable of receiving the superheated feed gas onto the leading edge and cracking a portion of non-methane hydrocarbons of the superheated feed gas into carbon oxides and hydrogen to form a heavy hydrocarbon reactor wet reformate comprising the associated gas stream methane, the carbon oxides, and the hydrogen; and a synthetic natural gas generator containing a second catalyst capable of receiving the heavy hydrocarbon reactor dry reformate to convert a portion of the carbon oxides and the hydrogen into converted methane to form a synthetic natural wet processed gas containing the associated gas stream methane and the converted methane, wherein the synthetic natural wet processed gas has an overall higher methane mole fraction than the associated gas stream.

In one embodiment, the heavy hydrocarbon reactor is an isothermal reactor. In another embodiment, the heavy hydrocarbon reactor is an adiabatic reactor.

In one embodiment, the system further includes a carbon dioxide removal apparatus capable of substantially removing carbon dioxide from the synthetic wet processed gas or a processed gas.

In another embodiment, the system further includes a water removal/recovery system capable of removing up to 100% of water vapor from at least one of the heavy hydrocarbon reactor wet reformate and the synthetic natural wet processed gas to form recovered water to replenish at least a portion of the system water consumed during chemical reactions within at least one of the heavy hydrocarbon reactor and the synthetic natural gas generator. The water removal/recovery system, upon detection of non-methane hydrocarbons above a predetermined threshold in the heavy hydrocarbon reactor wet reformate, may be designed to remove less than 100% of the water vapor from the heavy hydrocarbon reactor wet reformate to provide a sufficient water vapor within the synthetic natural gas generator to mitigate damage to the second catalyst. The system may include a system water mixing point capable of re-introducing the recovered water with a portion of tank water to form the system water.

In one embodiment, the system further includes a water removal/recovery system capable of: removing water vapor from the heavy hydrocarbon reactor wet reformate to form a first removed water portion and supplying the first removed water portion to the system water mixing point; remove water vapor from the synthetic natural wet processed gas to form a second removed water portion and supplying the second removed water portion to the system water mixing point; and supply tank water to the system water mixing point, wherein the system water mixing point is capable of mixing and purifying the first removed water portion, the second removed water portion, and the tank water to form the system water. In one embodiment, the total sum of the volume of the first removed water portion and the second removed water portion varies from about 0% to about 90% of the system water. In one embodiment, the volume of the tank water varies from about 10% to about 100% of the system water.

In one embodiment, the system further includes two or more recuperative heating systems capable of increasing water removal from the heavy hydrocarbon reactor wet reformate and the synthetic natural wet processed gas by: reducing a temperature of the heavy hydrocarbon reactor wet reformate prior to the removal of the water vapor from the heavy hydrocarbon reactor wet reformate such that a first removed water temperature of the first removed water portion is lower than the water boiling point temperature; and reducing the temperature of the synthetic natural wet processed gas prior to the removal of the water vapor from the synthetic natural wet processed gas such that a second removed water temperature of the second removed water portion is lower than the water boiling point temperature, wherein the temperature of the supply water is lower than the water boiling point temperature prior to entry of the supply water into the steam generator.

In one embodiment, the system further includes one or more recuperative heating systems capable of increasing a first temperature of the feed gas to a second higher temperature that is greater than the first temperature with heat from the heavy hydrocarbon reactor wet reformate prior to entry of the feed gas into the super heater, wherein a temperature of the heavy hydrocarbon reactor wet reformate decreases as it exits the one or more recuperative heating systems and the second higher temperature of the feed gas is increased above its boiling point.

In one embodiment, the gas conversion system includes one or more recuperative heating systems capable of increasing a temperature of a heavy hydrocarbon reactor dry reformate prior to entry into the synthetic natural gas generator with heat from a synthetic natural wet processed gas, wherein a temperature of the synthetic natural wet processed gas decreases as it exits the one or more recuperative heating systems.

In one embodiment, the system includes a thermal management system capable of extracting heat from at least one of the heavy hydrocarbon reactor wet reformate and the synthetic natural gas wet processed gas to increase temperatures of at least one of (i) the feed gas, and (ii) the heavy hydrocarbon reactor dry reformate, whereby energy demands of one or more of the burner management systems of the steam generator, super heater, heavy hydrocarbon reactor, and synthetic natural gas generator are reduced. The thermal management system may include at least two heat exchangers.

In one embodiment, the system includes at least one variable heat exchanger, at least one water knockout, and a non-methane hydrocarbon detector disposed in a fluid circuit between the heavy hydrocarbon reactor and the synthetic natural gas generator, wherein the at least one variable heat exchanger is capable of removing heat from the heavy hydrocarbon reactor wet reformate upstream of the at least one water knockout; wherein the at least one water knockout is disposed downstream of the at least one variable heat exchanger, and is capable of removing water from the heavy hydrocarbon reactor wet reformate; wherein the non-methane hydrocarbon detector is disposed downstream of the at least one water knockout, and is capable of measuring non-methane hydrocarbon levels in the heavy hydrocarbon reactor wet reformate; and a controller in communication with (i) the at least one variable heat exchanger, (ii) at least one temperature sensor of at least one water knockout, (iii) the non-methane hydrocarbon detector, and (iv) at least one or both burners of the heavy hydrocarbon reactor and the super heater, wherein the controller is capable of performing at least one of the following parameter adjustments when the temperature of at least one of the heavy hydrocarbon reactor wet reformate and the non-methane hydrocarbon levels in the heavy hydrocarbon reactor wet reformate exceeds predetermined threshold values: adjusting burner temperature of the burner of the heavy hydrocarbon reactor, adjusting burner temperature of the burner of the super heater, adjusting the at least one variable heat exchanger to compensate for an increase in temperature of the heavy hydrocarbon reactor wet reformate, and adjusting water vapor removal from the heavy hydrocarbon reactor wet reformate.

In one embodiment, the gas conversion system includes: at least one gas consuming unit capable of receiving the product gas; and a controller in communication with at least one of a feedback component positioned at a product gas inlet of the at least one gas consuming unit to form a closed loop control system, wherein the feedback component comprises at least one of a pressure sensor and a gas flow meter; wherein the controller is capable of adjusting system parameters to vary product gas production rate to match the fuel flow demand of the at least one gas consuming unit in real-time, on-demand based on measurements from the feedback component.

In one embodiment, the controller is capable of: monitoring fuel flow demand of the at least one gas consuming unit, and transmitting one or more command signals to one or more control devices of the gas conversion system in response to changes in the fuel flow demand as determined by the feedback component, whereby the production of product gas is controlled to match the fuel flow demand of the at least one gas consuming unit.

In one embodiment, the one or more command signals adjust output flow of the steam from the boiler in response to changes in pressure or changes in gas flow from the feedback component resulting from a change in fuel flow demand from the at least one gas consuming unit, wherein the output flow of the steam is adjusted to match product gas production with fuel flow demand by maintaining at least one of the pressure and the gas flow within predetermined threshold limits.

In one embodiment, the one or more command signals includes a command signal configured to adjust flow of feed gas in response to changes in the output flow of the steam from the steam generator, wherein the feed gas flow rate is adjusted to maintain a predetermined steam-to-carbon ratio within threshold limits In one embodiment, another one or more command signals is provided to adjust pressure of the system water in response to changes in the output flow of the steam from the boiler.

In one embodiment, the one or more command signals includes a command signal configured to adjust flow of feed gas in response to changes in pressure or changes in gas flow from the feedback component resulting from a change in fuel flow demand from the one or more gas consuming units, wherein the output flow of the feed gas is adjusted to match product gas production with fuel flow demand by maintaining at least one of the pressure and the gas flow within threshold limits.

In one embodiment, the one or more command signals includes a command signal configured to adjust flow of the steam from the boiler in response to changes in the flow rate of feed gas, wherein the flow rate of the steam from the boiler is adjusted to maintain a predetermined steam-to-carbon ratio within threshold limits.

In one embodiment, the controller further comprises an automated direct feedback control to vary a product gas production rate to match a fuel consumption rate of the one or more gas consuming units, wherein a measurement from the feedback component is a feedback mechanism to adjust flow rate of the heavy hydrocarbon reactor wet reformate to increase at least one of the pressure and flow rate at the product gas inlet of the one or more gas consuming units back to a predetermined level, thereby creating the required product gas production rate.

In one embodiment, the controller further comprises an automated direct feedback control to vary product gas production rate to match a fuel consumption rate of the at least one gas consuming unit, wherein a pressure measurement from the pressure sensor is a feedback mechanism to adjust flow rate of the heavy hydrocarbon reactor wet reformate to create the required product gas production rate.

In one embodiment, the system further includes an enrichment mixing valve system configured to mix a predetermined percentage of at least another portion of the associated gas stream with the processed gas in a ratio that creates a product gas stream with predetermined target values for at least one of methane number, heating value and composition.

In one embodiment, the predetermined percentage is adjusted based on measurement of at least one of heating value, methane number, and composition for one or more of the burner exhaust, associated gas stream, processed gas and product gas in order to maintain product gas within threshold limits for the predetermined target values. The system may further include a Flame Ionization Detector (FID) and an Infrared composition sensor to measure heating value of at least one of the heavy hydrocarbon reactor dry reformate, associated gas stream, feed gas, the processed gas, and the product gas.

The system may further include a purge system in fluid connectivity with one or more of the heavy hydrocarbon reactor and the synthetic natural gas generator for use during non-operation, startup, shutdown, and heat ups to supply an inert gas to purge hydrocarbons and any oxidizing agents from one or more of the heavy hydrocarbon reactor and the synthetic natural gas generator and to provide an inert gas blanket over reactor catalyst to prevent oxidation and formation of nickel carbonyl. In one embodiment, the inert gas is selected from the group comprising nitrogen and argon.

In one embodiment, the system further includes a Joule-Thomson (J-T) apparatus capable of receiving at least a portion of the associated gas stream and separating the at least a portion of the associated gas into (a) a J-T liquid containing primarily non-methane hydrocarbons, wherein the J-T liquid in gaseous form substitutes for the at least a portion of the associated gas stream being received by the mixing valve system, and (b) a J-T gas containing primarily methane and lessor amounts of non-methane hydrocarbons, wherein the J-T gas is blended with the product gas to form a second product gas.

The gas conversion system may further include a vaporizing apparatus configured to receive the J-T liquid and convert the J-T liquids to gaseous form, and supply the J-T liquids to the mixing valve system. In one embodiment the system includes a carbon dioxide removal apparatus capable of substantially removing carbon dioxide from the product gas to form a second product gas, wherein the J-T gas is blended with the second product gas to form a third product gas.

In one embodiment, the remaining portion of the associated gas stream is further blended with the third product gas to form the fourth product gas.

In one embodiment, the system includes: one or more gas consuming units capable of receiving the product gas as unit feed gas; and a controller in communication with a feedback component positioned at a fuel gas inlet for the one or more gas consuming units to form a closed loop control system, wherein the feedback component includes at least one of a pressure sensor and a gas flow meter; wherein the controller is capable of adjusting system parameters to vary product gas flow to match the fuel flow demand of the one or more gas consuming units in real-time, on-demand, based on measurements from the feedback component. The system may include one or more gas consuming units capable of receiving the product gas as unit feed gas; and a controller in communication with a feedback component positioned at a fuel gas inlet for one or more gas consuming units to form a closed loop control system, wherein the feedback component includes at least one of a pressure sensor and a gas flow meter; wherein the controller is capable of: monitoring fuel flow demand of the one or more gas consuming units, and transmitting one or more command signals to one or more control devices of the gas conversion system in response to changes in the fuel flow demand as determined by the feedback component; whereby the production of product gas is controlled to match the fuel flow demand of the one or more gas consuming units.

Regardless of whether or not the system includes a carbon dioxide removal apparatus, various embodiments also include the following embodiments.

In the one or more command signals adjust the feed gas flow rate in response to changes sensed by the feedback component resulting from a change in fuel flow demand from the one or more gas consuming units, wherein the flow rate of feed gas is adjusted to match product gas production with fuel flow demand by maintaining at least one of pressure and gas flow within predetermined threshold limits.

In one embodiment, the system further includes an enrichment system which mixes natural gas stream with product gas in an amount equal to a predetermined enrichment percent of the product gas such that the product meets predetermined target values for at least one of methane number, heating value and composition.

In one embodiment, the predetermined enrichment percent is adjusted based on measurement of the heating value, Methane Number and/or composition of product gas, product gas and/or natural gas stream in order to maintain the product gas within threshold limits of the predetermined target values.

In one embodiment, the one or more command signals includes a command signal configured to adjust natural gas stream flow rate in response to changes in a measurement from the feedback component resulting from changes in fuel flow demand from the one or more gas consuming units, whereby the flow rate of natural gas stream is adjusted to match product gas production with fuel flow demand by maintaining at least one of the pressure and the gas flow within threshold limits.

In one embodiment, the gas conversion system includes an enrichment system whereby product gas is mixed with natural gas stream in an amount equal to a predetermined enrichment percent of natural gas stream such that the product gas meets predetermined target values for at least one of methane number, heating value and composition.

In one embodiment, the enrichment system adjusts the flow rate of feed gas to control the production rate of the product gas in order to maintain the amount of product gas mixed with natural gas stream within threshold limits of the predetermined enrichment percent.

In one embodiment, the predetermined enrichment percent is adjusted based on measurement of the heating value, Methane Number and/or composition of product gas, product gas and/or natural gas stream in order to maintain product gas within threshold limits of the predetermined target values.

In one embodiment, the water removal/recovery system comprises multiples stages of water removal capable of increasing water removal from the heavy hydrocarbon reactor wet reformate and the synthetic natural wet processed gas by: reducing the amount of liquid water in the heavy hydrocarbon reactor wet reformate sent to a next set of heat exchanger and water removal device in series such that the heat transfer in the next heat exchanger is only used for the remaining water vapor; and reducing the amount of liquid water in the synthetic natural wet processed gas sent to a next set of heat exchanger and water removal device in series such that the heat transfer in the next heat exchanger is only used for the remaining water vapor.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various parameters (sometimes referred to as requirements) are described which may be appropriate for some embodiments but not for other embodiments.

From the foregoing, it will be appreciated that, although specific embodiments of the technology have been described herein for purposes of illustration, various modifications may be made without deviating from the spirit and scope of the technology. Further, certain aspects of the new technology described in the context of particular embodiments may be combined or eliminated in other embodiments. Moreover, while advantages associated with certain embodiments of the technology have been described in the context of those embodiments, other embodiments may also exhibit such advantages, and not all embodiments need necessarily exhibit such advantages to fall within the scope of the technology. Also, contemplated herein are methods which may include any procedural step inherent in the structures and systems described. Accordingly, the disclosure and associated technology can encompass other embodiments not expressly shown or described herein.

The terms used in this specification generally have their ordinary meanings in the art, within the context of the disclosure, and in the specific context where each term is used. It will be appreciated that the same thing can be said in more than one way. Consequently, alternative language and synonyms may be used for any one or more of the terms discussed herein, and any special significance is not to be placed upon whether or not a term is elaborated or discussed herein. Synonyms for some terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification. Unless otherwise defined, all technical and scientific terms used herein have the same meaning as commonly understood by one of ordinary skill in the art to which this disclosure pertains. In the case of conflict, the present document, including definitions, will control.

The invention claimed is:

1. A gas conversion system configured to form a second product gas from an associated gas stream, the gas conversion system comprising:
   a steam generator configured to receive system water and to output steam;
   a Joule-Thomson (J-T) apparatus configured (i) to receive at least a portion of an associated gas stream containing methane and non-methane hydrocarbons and (ii) to separate the at least a portion of the associated gas stream into:
      (a) a J-T liquid in gaseous form containing primarily non-methane hydrocarbons, and
      (b) a J-T gas containing primarily methane and lesser amounts of non-methane hydrocarbons;
   a mixing valve system configured to flow control at least a portion of the J-T liquid and the steam, and to output a feed gas which is a mixture of the steam and the at least a portion of the J-T liquid;
   a super heater configured to receive the feed gas and to superheat the feed gas to a predetermined temperature range to form a superheated feed gas;
   a heavy hydrocarbon reactor containing a first catalyst having a leading edge and configured to receive the superheated feed gas onto the leading edge and to crack a portion of the non-methane hydrocarbons of the superheated feed gas into carbon oxides and hydrogen to form a heavy hydrocarbon reactor reformate comprising methane in the J-T liquid from the associated gas stream, the carbon oxides, and the hydrogen; and
   a synthetic natural gas generator containing a second catalyst configured to receive the heavy hydrocarbon reactor reformate to convert a portion of the carbon oxides and the hydrogen into converted methane to form a synthetic natural wet processed gas containing the methane in the J-T liquid from the associated gas stream and the converted methane, wherein the synthetic natural wet processed gas has an overall higher methane mole fraction than the J-T liquid;
   wherein the gas conversion system is configured to blend (i) at least a portion of the synthetic natural wet processed gas as a product gas with (ii) the J-T gas to form the second product gas.

2. The gas conversion system according to claim 1, wherein the heavy hydrocarbon reactor is an isothermal reactor.

3. The gas conversion system according to claim 1, wherein the heavy hydrocarbon reactor is an adiabatic reactor.

4. The gas conversion system according to claim 1, further comprising a carbon dioxide removal apparatus configured to substantially remove carbon dioxide from the synthetic wet processed gas or the product gas.

5. The gas conversion system according to claim 1, wherein:
   the heavy hydrocarbon reactor reformate is a heavy hydrocarbon reactor wet reformate; and
   the gas conversion system further comprises a water removal/recovery system configured to remove up to 100% of water vapor from at least one of the heavy hydrocarbon reactor wet reformate and the synthetic natural wet processed gas to form recovered water to replenish at least a portion of the system water consumed during chemical reactions within at least one of the heavy hydrocarbon reactor and the synthetic natural gas generator.

6. The gas conversion system according to claim 5, wherein the water removal/recovery system, upon detection of non-methane hydrocarbons above a predetermined threshold in the heavy hydrocarbon reactor wet reformate, is configured to remove less than 100% of the water vapor from the heavy hydrocarbon reactor wet reformate to provide a sufficient water vapor within the synthetic natural gas generator to mitigate damage to the second catalyst.

7. The gas conversion system according to claim 5, further comprising a system water mixing point configured to re-introduce the recovered water with a portion of tank water to form the system water.

8. The gas conversion system according to claim 7, wherein the water removal/recovery system is further configured to:
  remove water vapor from the heavy hydrocarbon reactor wet reformate to form a first removed water portion and to supply the first removed water portion to the system water mixing point;
  remove water vapor from the synthetic natural wet processed gas to form a second removed water portion and to supply the second removed water portion to the system water mixing point; and
  supply the tank water to the system water mixing point, wherein the system water mixing point is configured to mix and to purify the first removed water portion, the second removed water portion, and the tank water to form the system water.

9. The gas conversion system according to claim 8, wherein the total volume of the first removed water portion and the second removed water portion is in a range from about 0% to about 90% of the volume of the system water.

10. The gas conversion system according to claim 8, wherein the volume of the tank water is in a range from about 10% to about 100% of the volume of the system water.

11. The gas conversion system according to claim 8, further comprising two or more recuperative heating systems configured to increase water removal from the heavy hydrocarbon reactor wet reformate and the synthetic natural wet processed gas by:
  being configured to reduce a temperature of the heavy hydrocarbon reactor wet reformate prior to the removal of the water vapor from the heavy hydrocarbon reactor wet reformate such that a first removed water temperature of the first removed water portion is lower than the water boiling point temperature; and
  being configured to reduce the temperature of the synthetic natural wet processed gas prior to the removal of the water vapor from the synthetic natural wet processed gas such that a second removed water temperature of the second removed water portion is lower than the water boiling point temperature,
  wherein the temperature of the supply water is lower than the water boiling point temperature prior to entry of the supply water into the steam generator.

12. The gas conversion system according to claim 11, wherein the water removal/recovery system comprises multiples stages of water removal configured to increase water removal from the heavy hydrocarbon reactor wet reformate and the synthetic natural wet processed gas by:
  being configured to reduce the amount of liquid water in the heavy hydrocarbon reactor wet reformate sent to a next set of heat exchanger and water removal device in series such that the heat transfer in the next heat exchanger is only used for the remaining water vapor; and
  being configured to reduce the amount of liquid water in the synthetic natural wet processed gas sent to a next set of heat exchanger and water removal device in series such that the heat transfer in the next heat exchanger is only used for the remaining water vapor.

13. The gas conversion system according to claim 1, further comprising one or more recuperative heating systems configured to increase a first temperature of the feed gas to a second higher temperature that is greater than the first temperature with heat from a heavy hydrocarbon reactor wet reformate prior to entry of the feed gas into the super heater, wherein a temperature of the heavy hydrocarbon reactor wet reformate decreases as it exits the one or more recuperative heating systems and the second higher temperature of the feed gas is increased above its boiling point.

14. The gas conversion system according to claim 1, further comprising one or more recuperative heating systems configured to increase a temperature of a heavy hydrocarbon reactor dry reformate prior to entry into the synthetic natural gas generator with heat from a synthetic natural wet processed gas, wherein a temperature of the synthetic natural wet processed gas decreases as it exits the one or more recuperative heating systems.

15. The gas conversion system according to claim 1, further comprising a thermal management system configured to extract heat from at least one of a heavy hydrocarbon reactor wet reformate and the synthetic natural gas wet processed gas to increase temperatures of at least one of (i) the feed gas, and (ii) a heavy hydrocarbon reactor dry reformate, whereby energy demands of one or more of the burner management systems of the steam generator, super heater, heavy hydrocarbon reactor, and synthetic natural gas generator are reduced.

16. The gas conversion system according to claim 15, wherein the thermal management system comprises at least two heat exchangers.

17. The gas conversion system according to claim 1, further comprising:
  at least one variable heat exchanger, at least one water knockout, and a non-methane hydrocarbon detector disposed in a fluid circuit between the heavy hydrocarbon reactor and the synthetic natural gas generator, wherein the at least one variable heat exchanger is configured to remove heat from a heavy hydrocarbon reactor wet reformate upstream of the at least one water knockout; wherein the at least one water knockout is disposed downstream of the at least one variable heat exchanger, and is configured to remove water from the heavy hydrocarbon reactor wet reformate; wherein the non-methane hydrocarbon detector is disposed downstream of the at least one water knockout, and is configured to measure non-methane hydrocarbon levels in the heavy hydrocarbon reactor wet reformate; and
  a controller in communication with (i) the at least one variable heat exchanger, (ii) at least one temperature sensor of at least one water knockout, (iii) the non-methane hydrocarbon detector, and (iv) at least one or both burners of the heavy hydrocarbon reactor and the super heater, wherein the controller is configured to perform at least one of the following parameter adjustments when the temperature of at least one of the heavy hydrocarbon reactor wet reformate and the non-methane hydrocarbon levels in the heavy hydrocarbon reactor wet reformate exceeds predetermined threshold values:
   a. adjustment of burner temperature of the burner of the heavy hydrocarbon reactor,
   b. adjustment of burner temperature of the burner of the super heater,
   c. adjustment of the at least one variable heat exchanger to compensate for an increase in temperature of the heavy hydrocarbon reactor wet reformate, and
   d. adjustment of water vapor removal from the heavy hydrocarbon reactor wet reformate.

18. The gas conversion system according to claim 1, further comprising:
   at least one gas consuming unit configured to receive the product gas; and
   a controller in communication with at least one of a feedback component positioned at a product gas inlet of the at least one gas consuming unit to form a closed loop control system,
   wherein the feedback component comprises at least one of a pressure sensor and a gas flow meter; wherein the controller is configured to adjust system parameters to vary product gas production rate to match the fuel flow demand of the at least one gas consuming unit in real-time, on-demand based on measurements from the feedback component.

19. The gas conversion system according to claim 18, wherein the controller is configured to:
   monitor fuel flow demand of the at least one gas consuming unit, and
   transmit one or more command signals to one or more control devices of the gas conversion system in response to changes in the fuel flow demand as determined by the feedback component,
   whereby the production of product gas is controlled to match the fuel flow demand of the at least one gas consuming unit.

20. The gas conversion system according to claim 19, wherein the one or more command signals are configured to adjust output flow of the steam from the boiler in response to changes in pressure or changes in gas flow from the feedback component resulting from a change in fuel flow demand from the at least one gas consuming unit, wherein the output flow of the steam is adjusted to match product gas production with fuel flow demand by maintaining at least one of the pressure and the gas flow within predetermined threshold limits.

21. The gas conversion system according to claim 20, wherein the one or more command signals includes a command signal configured to adjust flow of feed gas in response to changes in the output flow of the steam from the steam generator, wherein the feed gas flow rate is adjusted to maintain a predetermined steam-to-carbon ratio within threshold limits.

22. The gas conversion system according to claim 20, further comprising another one or more command signals configured to adjust pressure of the system water in response to changes in the output flow of the steam from the boiler.

23. The gas conversion system according to claim 19, wherein the one or more command signals includes a command signal configured to adjust flow of feed gas in response to changes in pressure or changes in gas flow from the feedback component resulting from a change in fuel flow demand from the one or more gas consuming units, wherein the output flow of the feed gas is adjusted to match product gas production with fuel flow demand by maintaining at least one of the pressure and the gas flow within threshold limits.

24. The gas conversion system according to claim 23, wherein the one or more command signals includes a command signal configured to adjust flow of the steam from the boiler in response to changes in the flow rate of feed gas, wherein the flow rate of the steam from the boiler is adjusted to maintain a predetermined steam-to-carbon ratio within threshold limits.

25. The gas conversion system according to claim 18, wherein the controller further comprises an automated direct feedback control configured to vary a product gas production rate to match a fuel consumption rate of the one or more gas consuming units, wherein a measurement from the feedback component is a feedback mechanism to adjust flow rate of a heavy hydrocarbon reactor wet reformate configured to increase at least one of the pressure and flow rate at the product gas inlet of the one or more gas consuming units back to a predetermined level, thereby creating the required product gas production rate.

26. The gas conversion system according to claim 18, wherein the controller further comprises an automated direct feedback control configured to vary product gas production rate to match a fuel consumption rate of the at least one gas consuming unit, wherein a pressure measurement from the pressure sensor is a feedback mechanism configured to adjust flow rate of a heavy hydrocarbon reactor wet reformate to create the required product gas production rate.

27. The gas conversion system according to claim 1, further comprising an enrichment mixing valve system configured to mix a predetermined percentage of at least another portion of the associated gas stream with the processed gas in a ratio that creates a product gas stream with predetermined target values for at least one of methane number, heating value and composition.

28. The gas conversion system according to claim 27, wherein the predetermined percentage is adjusted based on measurement of at least one of heating value, methane number, and composition for one or more of the burner exhaust, associated gas stream, processed gas and product gas in order to maintain product gas within threshold limits for the predetermined target values.

29. The gas conversion system according to claim 28, further comprising a Flame Ionization Detector (FID) and an Infrared composition sensor configured to measure heating value of at least one of a heavy hydrocarbon reactor dry reformate, the associated gas stream, the feed gas, the processed gas, and the product gas.

30. The gas conversion system according to claim 1, further comprising a purge system in fluid connectivity with one or more of the heavy hydrocarbon reactor and the synthetic natural gas generator configured for use during non-operation, startup, shutdown, and heat ups to supply an inert gas to purge hydrocarbons and any oxidizing agents from one or more of the heavy hydrocarbon reactor and the synthetic natural gas generator and to provide an inert gas blanket over reactor catalyst to prevent oxidation and formation of nickel carbonyl.

31. The gas conversion system according to claim 30, wherein the inert gas is selected from the group consisting of nitrogen and argon.

32. The gas conversion system according to claim 5, further comprising a purge system in fluid connectivity with the water removal/recovery system configured to provide an inert gas for de-aeration of recovered water, whereby the use of oxygen scavenging chemicals is reduced.

33. The gas conversion system according to claim 32, wherein the inert gas is selected from the group consisting of nitrogen and argon.

34. The gas conversion system of claim 1, further comprising a vaporizing apparatus configured to receive the J-T liquid and convert the J-T liquids to gaseous form, and to supply the J-T liquid to the mixing valve system.

35. The gas conversion system of claim 1, further comprising a carbon dioxide removal apparatus configured to substantially remove carbon dioxide from the product gas.

36. The gas conversion system according to claim 1, further comprising:
one or more gas consuming units configured to receive the product gas as a unit feed gas; and
a controller in communication with a feedback component positioned at a fuel gas inlet for the one or more gas consuming units to form a closed loop control system, wherein the feedback component includes at least one of a pressure sensor and a gas flow meter;
wherein the controller is configured to adjust system parameters to vary product gas flow to match the fuel flow demand of the one or more gas consuming units in real-time, on-demand, based on measurements from the feedback component.

37. The gas conversion system according to claim 36, wherein the controller is configured to adjust the feed gas flow rate in response to changes sensed by the feedback component resulting from a change in the fuel flow demand from the one or more gas consuming units, wherein the flow rate of the feed gas is adjusted to match product gas production with fuel flow demand by maintaining at least one of pressure and gas flow within predetermined threshold limits.

38. The gas conversion system according to claim 37, further comprising an enrichment system configured to mix the associated gas stream with the second product gas in an amount equal to a predetermined enrichment percent of the second product gas such that a resulting third product gas meets predetermined target values for at least one of methane number, heating value and composition.

39. The gas conversion system according to claim 38, wherein the predetermined enrichment percent is adjusted based on measurement of the heating value, methane number and/or composition of the product gas, the second product gas and/or the associated gas stream in order to maintain the third product gas within threshold limits of the predetermined target values.

40. The gas conversion system according to claim 36, wherein the controller is configured to adjust the associated gas stream flow rate in response to changes in a measurement from the feedback component resulting from changes in the fuel flow demand from the one or more gas consuming units, whereby the flow rate of associated gas stream is adjusted to match product gas production with fuel flow demand by maintaining at least one of the pressure and the gas flow within threshold limits.

41. The gas conversion system according to claim 40, further comprising an enrichment system configured to mix the second product gas with the associated gas stream in an amount equal to a predetermined enrichment percent of the associated gas stream such that a resulting third product gas meets predetermined target values for at least one of methane number, heating value, and composition.

42. The gas conversion system according to claim 41, wherein the enrichment system is configured to adjust the flow rate of feed gas to control the production rate of the second product gas in order to maintain the amount of the second product gas mixed with the associated gas stream within threshold limits of the predetermined enrichment percent.

43. The gas conversion system according to claim 42, wherein the predetermined enrichment percent is adjusted based on measurement of the heating value, methane number and/or composition of the product gas, the second product gas and/or the associated gas stream in order to maintain the third product gas within threshold limits of the predetermined target values.

44. The gas conversion system according to claim 1, further comprising:
one or more gas consuming units configured to receive the product gas as a unit feed gas; and
a controller in communication with a feedback component positioned at a fuel gas inlet for one or more gas consuming units to form a closed loop control system, wherein the feedback component includes at least one of a pressure sensor and a gas flow meter;
wherein the controller is configured to:
monitor fuel flow demand of the one or more gas consuming units, and
transmit one or more command signals to one or more control devices of the gas conversion system in response to changes in the fuel flow demand as determined by the feedback component;
whereby the production of product gas is controlled to match the fuel flow demand of the one or more gas consuming units.

45. The gas conversion system according to claim 44, wherein the one or more command signals are configured to adjust the feed gas flow rate in response to changes sensed by the feedback component resulting from a change in the fuel flow demand from the one or more gas consuming units, wherein the flow rate of the feed gas is adjusted to match product gas production with fuel flow demand by maintaining at least one of pressure and gas flow within predetermined threshold limits.

46. The gas conversion system according to claim 45, further comprising an enrichment system configured to mix the associated gas stream with the second product gas in an amount equal to a predetermined enrichment percent of the second product gas such that a resulting third product gas meets predetermined target values for at least one of methane number, heating value and composition.

47. The gas conversion system according to claim 46, wherein the predetermined enrichment percent is adjusted based on measurement of the heating value, methane number and/or composition of the product gas, the second product gas and/or the associated gas stream in order to maintain the third product gas within threshold limits of the predetermined target values.

48. The gas conversion system according to claim 44, wherein the one or more command signals are configured to adjust the associated gas stream flow rate in response to changes in a measurement from the feedback component resulting from changes in the fuel flow demand from the one or more gas consuming units, whereby the flow rate of associated gas stream is adjusted to match product gas production with the fuel flow demand by maintaining at least one of the pressure and the gas flow within threshold limits.

49. The gas conversion system according to claim 48, further comprising an enrichment system configured to mix the second product gas is mixed with the associated gas stream in an amount equal to a predetermined enrichment percent of the associated gas stream such that a resulting third product gas meets predetermined target values for at least one of methane number, heating value and composition.

50. The gas conversion system according to claim 49, wherein the enrichment system is configured to adjust the flow rate of feed gas to control the production rate of the second product gas in order to maintain the amount of the second product gas mixed with the associated gas stream within threshold limits of the predetermined enrichment percent.

51. The gas conversion system according to claim 50, wherein the predetermined enrichment percent is adjusted based on measurement of the heating value, methane number, and/or composition of the product gas, the second product gas and/or the associated gas stream in order to maintain the third product gas within threshold limits of the predetermined target values.

* * * * *